US011191798B2

(12) United States Patent
Su et al.

(10) Patent No.: US 11,191,798 B2
(45) Date of Patent: Dec. 7, 2021

(54) **EXTRACTS OF *ANDROGRAPHIS PANICULATA*, METHODS FOR PREPARATION AND USE THEREOF**

(71) Applicant: NUTRITION SCIENCE PARTNERS LIMITED, Hong Kong (CN)

(72) Inventors: Wei-Guo Su, Shanghai (CN); Xiong Li, Shanghai (CN); Weihan Zhang, Shanghai (CN); Bo Liu, Shanghai (CN); Huaqing Cai, Shanghai (CN); Zhilong Weng, Shanghai (CN); Hongqiang Wang, Shanghai (CN); Zhiyong Yu, Shanghai (CN); Lei Jiang, Shanghai (CN)

(73) Assignee: NUTRITION SCIENCE PARTNERS LIMITED, Hong Kong (CN)

( * ) Notice: Subject to any disclaimer, the term of this patent is extended or adjusted under 35 U.S.C. 154(b) by 192 days.

(21) Appl. No.: 16/344,914

(22) PCT Filed: Nov. 1, 2017

(86) PCT No.: PCT/CN2017/108942
§ 371 (c)(1),
(2) Date: Apr. 25, 2019

(87) PCT Pub. No.: WO2018/082568
PCT Pub. Date: May 11, 2018

(65) Prior Publication Data
US 2019/0240275 A1     Aug. 8, 2019

Related U.S. Application Data

(63) Continuation-in-part of application No. PCT/CN2016/104384, filed on Nov. 2, 2016.

(51) Int. Cl.
| | | |
|---|---|---|
| *A61K 36/19* | (2006.01) |
| *A61K 31/365* | (2006.01) |
| *A61P 1/00* | (2006.01) |
| *A61P 29/00* | (2006.01) |
| *A61P 11/06* | (2006.01) |
| *A61P 11/00* | (2006.01) |
| *A61P 35/00* | (2006.01) |
| *A61P 37/02* | (2006.01) |
| *A61P 17/06* | (2006.01) |
| *A61P 37/00* | (2006.01) |

(52) U.S. Cl.
CPC ............ *A61K 36/19* (2013.01); *A61K 31/365* (2013.01); *A61P 1/00* (2018.01); *A61P 11/00* (2018.01); *A61P 11/06* (2018.01); *A61P 17/06* (2018.01); *A61P 29/00* (2018.01); *A61P 35/00* (2018.01); *A61P 37/00* (2018.01); *A61P 37/02* (2018.01)

(58) Field of Classification Search
CPC .. A61K 31/365; A61K 36/19; A61K 31/7048; A61P 1/00; A61P 1/04; A61P 1/18; A61P 29/00; A61P 11/06; A61P 17/00; A61P 17/06; A61P 1/02; A61P 21/00; A61P 25/28; A61P 27/02; A61P 31/04; A61P 31/18; A61P 35/02; A61P 37/02; A61P 37/04; A61P 37/06; A61P 3/10; A61P 9/04; A61P 1/06

See application file for complete search history.

(56) References Cited

U.S. PATENT DOCUMENTS

| 2014/0271923 A1 | 9/2014 | Reid |
| 2015/0182570 A1 | 7/2015 | Weng et al. |

FOREIGN PATENT DOCUMENTS

| CN | 1548041 A | 11/2004 |
| CN | 1689628 A | 11/2005 |
| CN | 1695702 A | 11/2005 |
| CN | 1810240 A | 8/2006 |
| CN | 1864704 A | 11/2006 |
| CN | 1921872 A | 2/2007 |
| CN | 101028318 A | 9/2007 |
| CN | 101040883 A | 9/2007 |
| CN | 101422494 A | 5/2009 |
| CN | 101559088 A | 10/2009 |
| CN | 102382083 A | 3/2012 |
| CN | 102652762 A | 9/2012 |
| CN | 103006724 A | 4/2013 |
| CN | 103585208 A | 2/2014 |
| CN | 104311515 A | 1/2015 |
| CN | 104382968 A | 3/2015 |
| CN | 105031622 A | 11/2015 |
| CN | 105294618 A | 2/2016 |
| CN | 105467023 A | 4/2016 |
| IN | 200901634 I1 | * 10/2011 |
| WO | WO-2005104722 A2 | 11/2005 |
| WO | WO-2006008115 A1 | 1/2006 |
| WO | WO-2008084283 A2 | 7/2008 |
| WO | WO-2009059158 A1 | 5/2009 |

OTHER PUBLICATIONS

English Translation of "Research Progress of Total Lactones of Andrographis paniculate", Lishizhen Medicine and Materia Medica Research, 2012, vol. 23, No. 11, p. 2854-2857, doi: 10.3969/j.issn. 1008-0805.2012.11.089.

International Search Report issued in PCT/CN2017/108942 dated Feb. 2, 2018.

Beck, et al., Growth Factors in Inflammatory Bowel Disease, Inflammatory Bowel Disease, 1999, 5:1:44-60.

Laddha, et al., Effect of Enzymes on Extraction of Andrographolide From Andrographis Paniculata Nees, International Journal of Pharma and Bio Sciences, 2010, 1-7.

Lin, et al., Alleviation of Experimental Ulcerative Colitis with the Synthetic Peptide, F2A4-K-NS (Fibratide). Dig Dis Sci, 2007, 52:2054-2062.

(Continued)

*Primary Examiner* — Aaron J Kosar
(74) *Attorney, Agent, or Firm* — Blank Rome LLP

(57) ABSTRACT

Disclosed herein are extracts of *Andrographis paniculata* having highly concentrated active ingredients, preparation methods and medical use for treating autoimmunity and inflammatory disease.

15 Claims, 7 Drawing Sheets

Specification includes a Sequence Listing.

(56) References Cited

OTHER PUBLICATIONS

Ová, et al., Antitussive Arabinoglactan of Andrographics Paniculata Demonstrates Synergistic Effect with Andrographolide, International Journal of Biological Macromolecules, 2014, 69:151-157.

Qiang Gao, Basic and Clinical Aspects of Mucosal Inflammation and Healing in Crohn's Disease, 1961, 124 pages.

Sun, et al., Transfection with aFGF cDNA Improves Wound Healing, The Society for Investigative Dermatology, Inc., 1997, 313-318.

Xu, et al., Synergetic effect of Andrographis paniculata polysaccharide on diabetic nephropathy with andrographolide, International Journal of Biological Macromolecules, 2012, 51:738-742.

李志亨等, "穿心莲总内酯的研究进展", 时珍国医国药 (Lishizhen Medicine and Materia Medica Research), 2012, vol. 23, No. 11, p. 2854-2857, doi: 10.3969/j.issn.1008-0805.2012.11.089.

Sandborn, et al., Andrographis paniculata Extract (HMPL-004) for Active Ulcerative Colitis, The American Journal of Gastroenterology, 2013, 108:90-98.

* cited by examiner

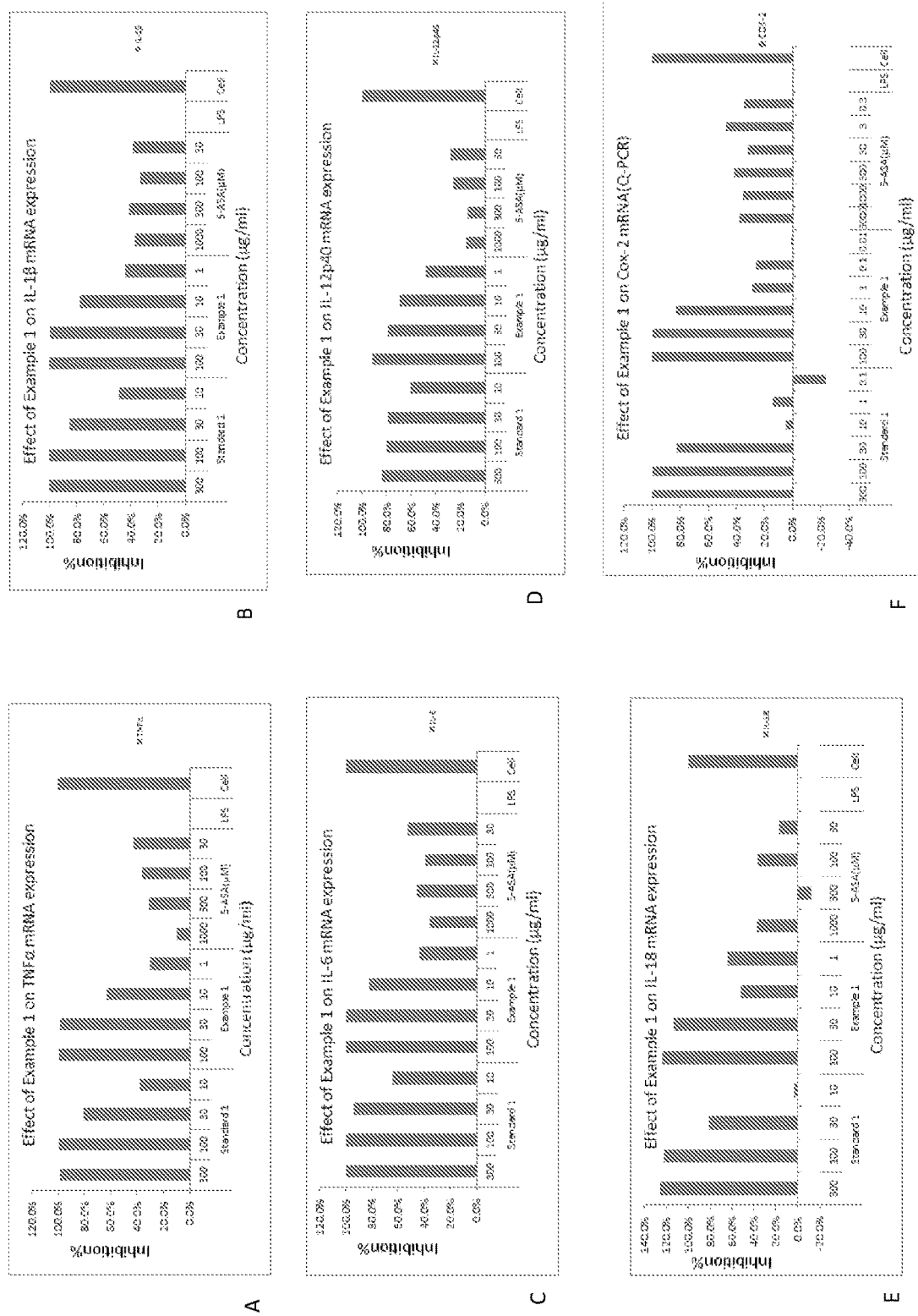
Figure1. Effect of Example 1 on LPS induced mRNA expression of pro-inflammatory factors. A. TNFα; B. IL-1β; C. IL-6; D. IL-12p40; E. IL-18; F. Cox-2

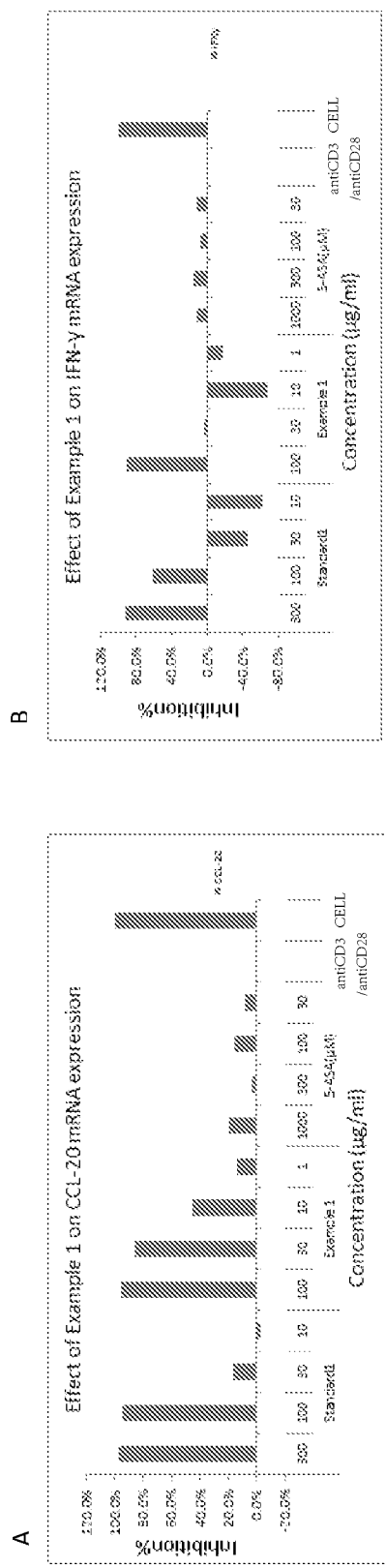
Figure 2. The effect of Example 1 on mRNA expression of pro-inflammatory factors induced by antiCD3 mAb / antiCD28 mAb in human PBMCs. A. CCL-20; B. IFNγ.

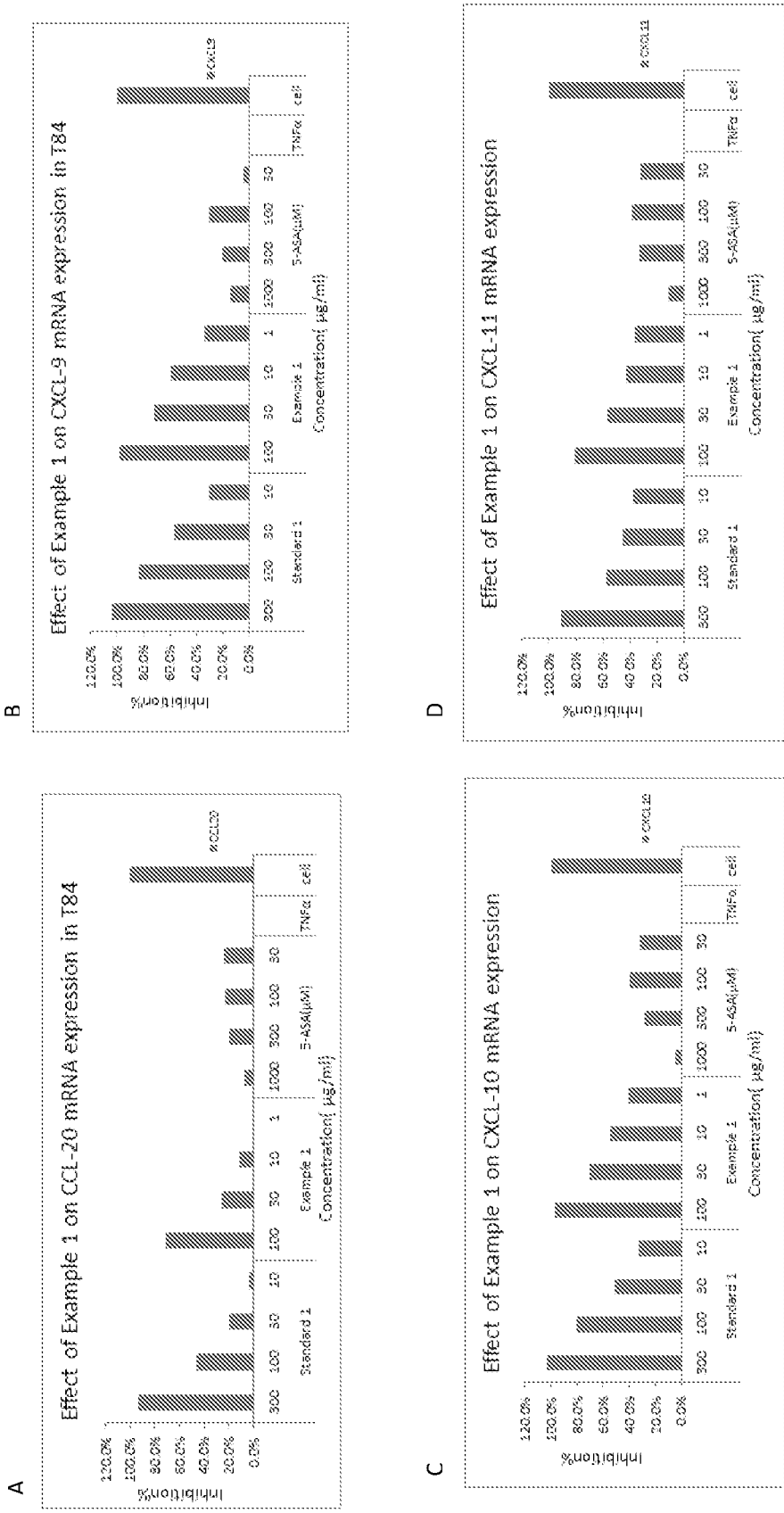
Figure3. Effect of Example 1 on chemokine mRNA expression in T84 cell line. A. CCL-20; B. CXCL-9; C. CXCL-10; D. CXCL-11.

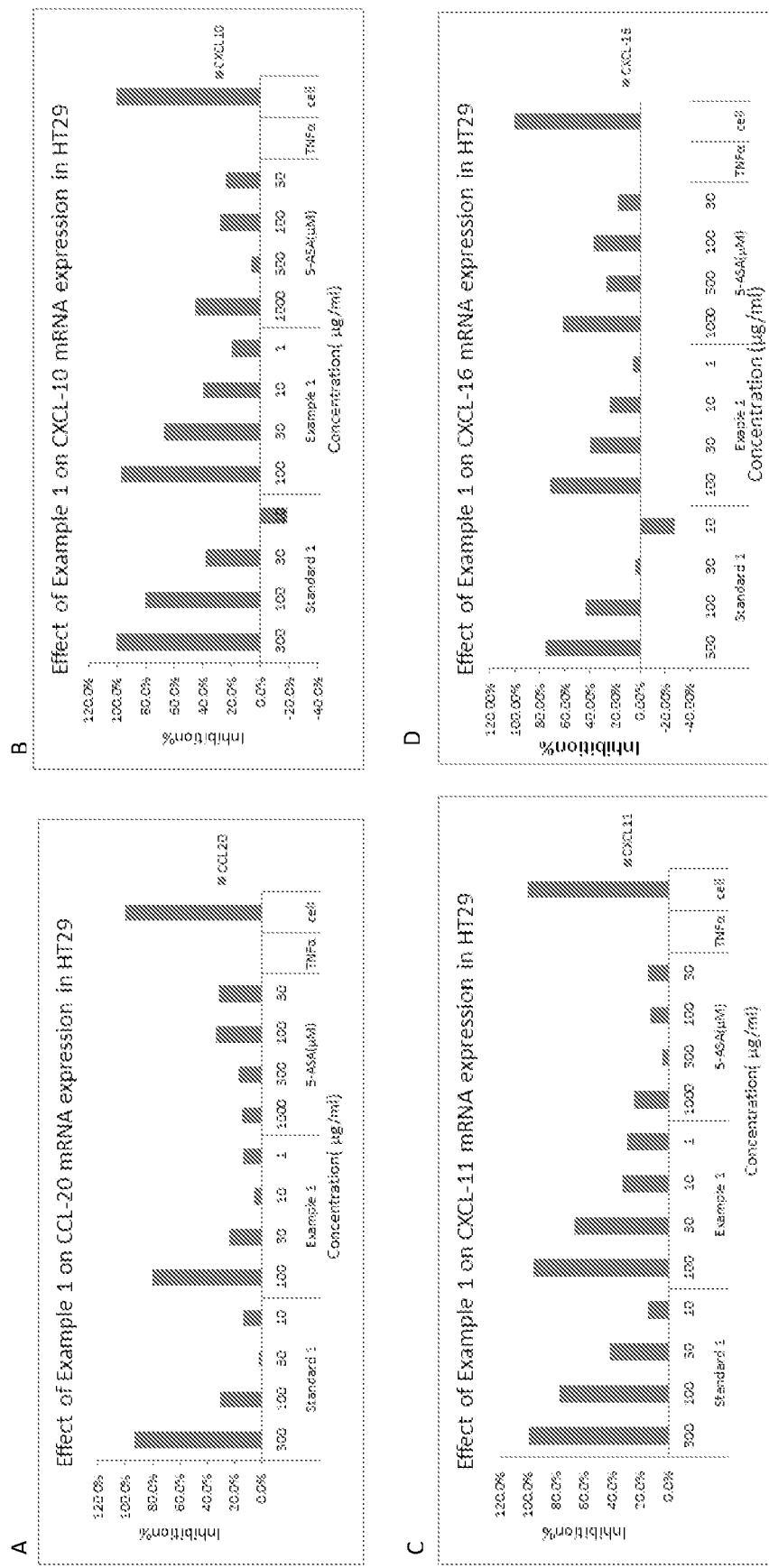
Figure4. Effect of Example 1 on chemokine mRNA expression in HT29 cell line. A. CCL-20; B. CXCL-10; C. CXCL-11; D. CXCL-16.

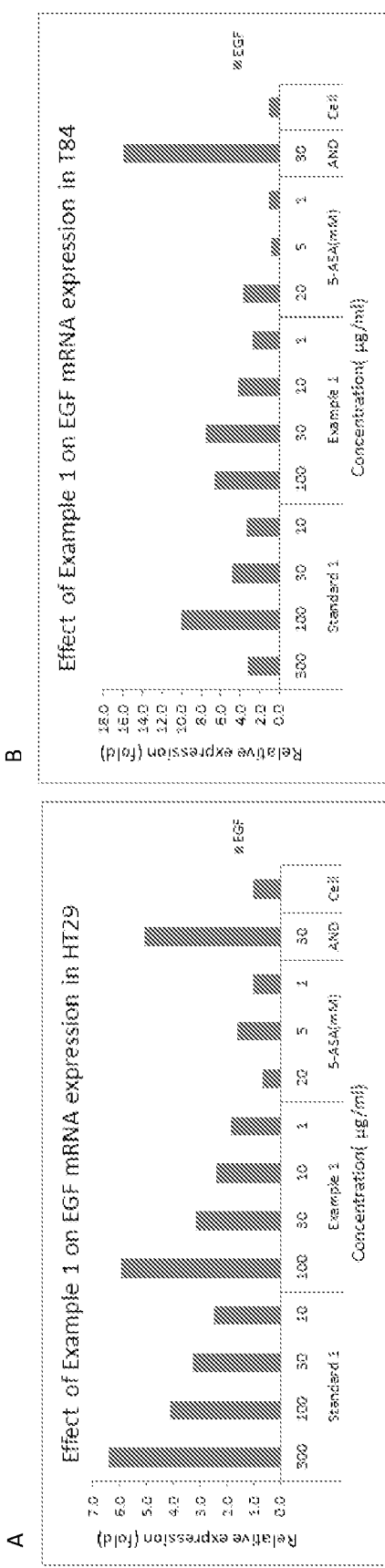
Figure 5. Effect of Example 1 on EGF mRNA expression in epithelial cell lines HT29 and T84
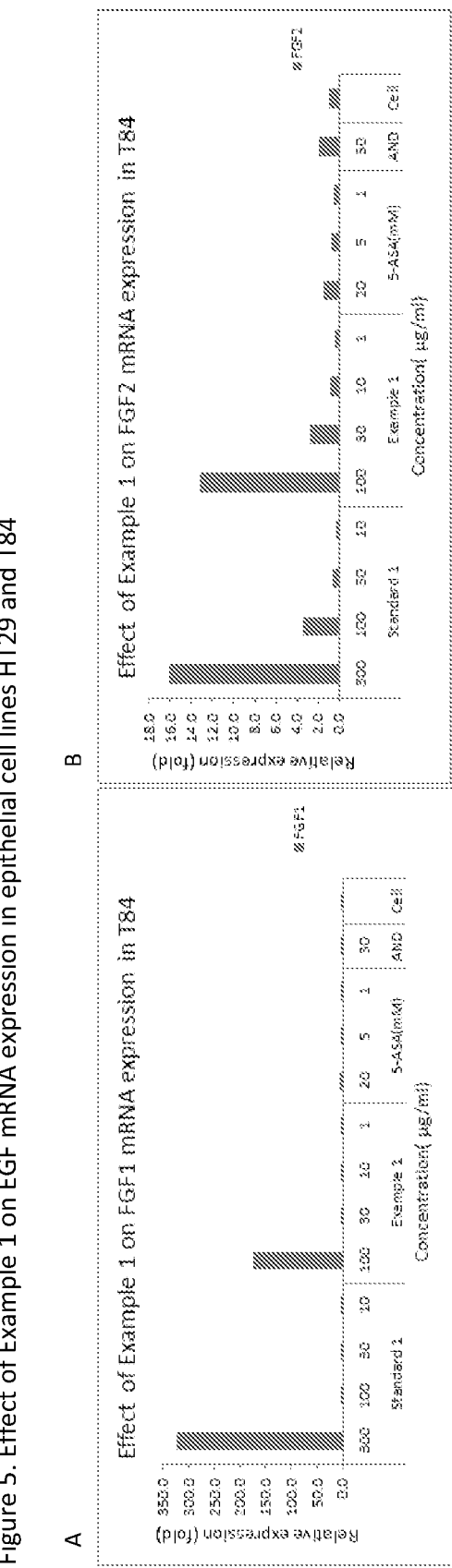
Figure 6. Effect of Example 1 on FGF1 and FGF2 mRNA expression in epithelial cell T84

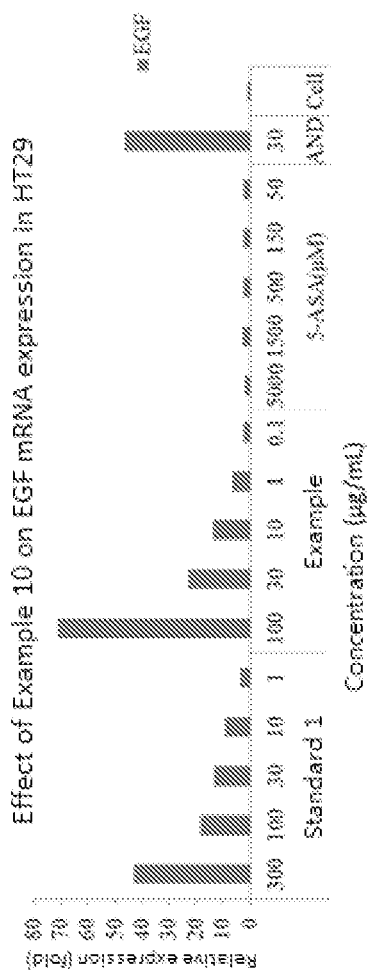
Figure 7 Effect of Example 10 on EGF mRNA expression in epithelial cell line HT29
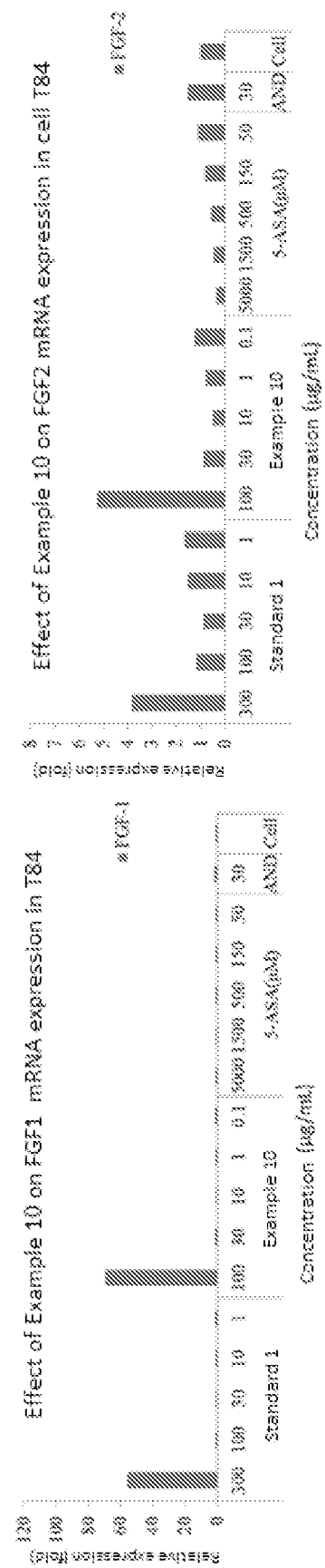
Figure 8 Effect of Example 10 on FGF1 and FGF2 mRNA expression in epithelial cell T84

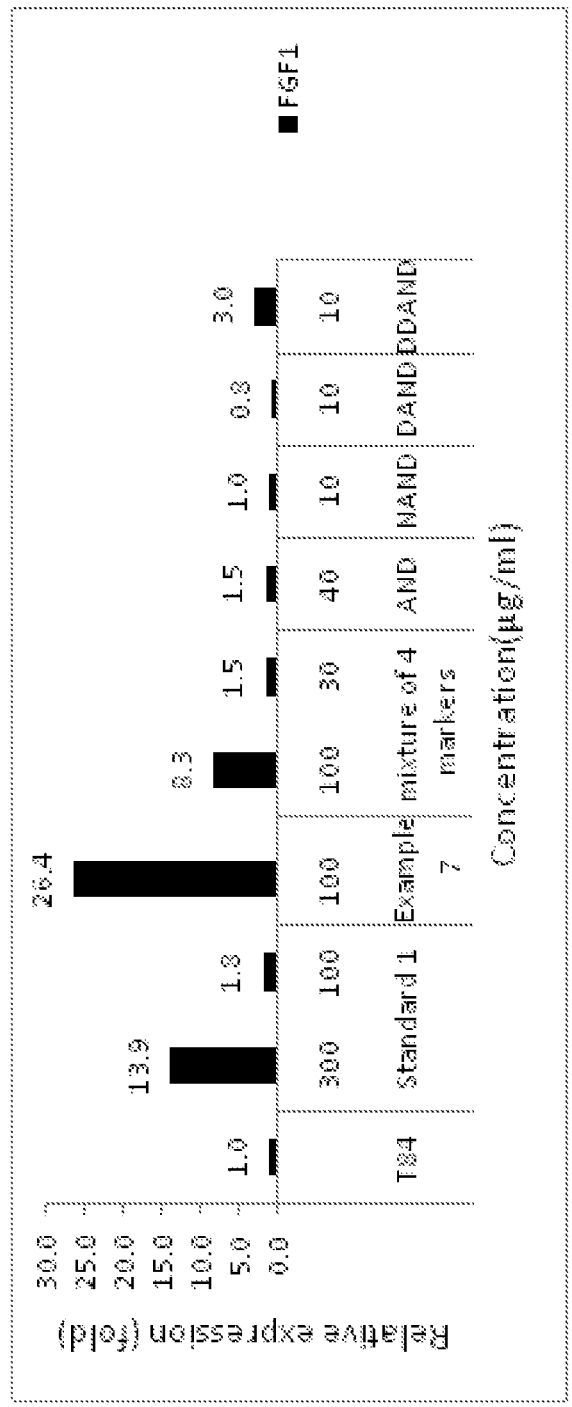
Figure 9. Effect of Example 7 on FGF1 mRNA expression in epithelial cell line T84

EXTRACTS OF *ANDROGRAPHIS PANICULATA*, METHODS FOR PREPARATION AND USE THEREOF

This application is the U.S. national stage of International Patent Application No. PCT/CN2017/108942, filed Nov. 1, 2017, which is a continuation-in-part of International Patent Application No. PCT/CN2016/104384, filed Nov. 2, 2016.

Disclosed herein are extracts of *Andrographis paniculata*, preparation methods and medical use thereof.

Chuanxinlian, the dried aerial part of *Andrographis paniculata* (Burm.f.) Nees from Acanthaceae plant, is widely distributed in Asia, such as China, India etc. . . . As a traditional Chinese medicine, Chuanxinlian has been used clinically in the treatment of respiratory tract infections, acute dysentery, gastroenteritis, fever and flu, hypertension, and other diseases.

The active ingredients in Chuanxinlian are reported to include Andrographolide lactones selected from, for example, andrographolide (AND), neoandrographolide (NAND), 14-deoxy-andrographolide (DAND), and 14-deoxy-11,12-dehydroandrographolide (DDAND), etc. Many processes have been developed to extract the active ingredients from *Andrographis paniculata*.

WO 2009/059158 discloses a preparation method of *Andrographis paniculata* extract, comprising the following steps: reflux-extracting dried aerial part of *Andrographis paniculata* with 90% ethanol, collecting the ethanol phase, and then extracting the solid residue with 90% ethanol again, combining the ethanol extracts, removing the solvent ethanol, adding dextrin and then drying and grinding, to obtain the *Andrographis paniculata* extract. The *Andrographis paniculata* extract comprises, by weight relative to the weight of the extract, 10-22% total andrographolide lactones, wherein AND, DAND, DDAND and NAND are, for example, 6-10%, 0.01-2%, 2-4% and 2-4%, respectively.

Nuclear factor κB (NF-κB) represents a family of structurally related transcription factors, such as RelA (p65), RelB, c-Rel, NF-κB1 (p50), and NF-κB2 (p52), which form as hetero- or homo-dimers that transactivate a large number of genes via binding to a κB promoter. They are pivotal regulators of innate and adaptive immune responses since their target genes are involved in a broad spectrum of biological functions, from immune cell proliferation, differentiation, maturation to activation. For example, NF-κB plays a crucial role in the establishment of immune tolerance, including both central tolerance and the peripheral function of regulatory T (Treg) cells. Therefore, dysregulation of NF-κB is believed to contribute to the pathogenesis of chronic inflammation of autoimmune diseases.

Activation of NF-κB has long been considered a prototypical proinflammatory signaling pathway, largely based on the activation of NF-κB by proinflammatory cytokines such as interleukin 1β (IL-1β) and tumor necrosis factor α (TNF-α). Furthermore, activation of NF-κB up-regulates many proinflammatory mediators including cytokines, chemokines and cell adhesion molecules. Together with IL-1β and TNF-α, those proinflammatory mediators play important roles in the pathogenesis of chronic inflammatory diseases such as rheumatoid arthritis (RA), inflammatory bowel disease (IBD), psoriasis, systemic lupus erythematosus (SLE), asthma, and chronic obstructive pulmonary disease (COPD). Thus, inhibition of NF-κB signaling pathway is a potentially great therapeutic approach for autoimmunity and inflammatory diseases.

IL-1β and TNF-α are key proinflammatory cytokines in chronic inflammation of autoimmune diseases. Several neutralization antibodies of TNF-a (such as Humira) and a soluble TNF-α receptor (Enbrel) have been approved for clinical treatment of autoimmune diseases including RA and IBD. Like TNF-α, IL-1β is produced in response to inflammatory stimuli and mediates various physiologic responses via activation of its receptor IL-1R to initiate signaling cascade, including inflammatory and immunologic reactions. As consequence in RA, for example, IL-1β additionally stimulates bone resorption and induces tissue damage like cartilage degradation as a result of loss of proteoglycans. In those RA patients, the concentrations of natural IL-1R receptor antagonist (IL-1Ra) in synovium are not high enough to counteract the elevated IL-1β concentrations.

Anakinra (Kineret), a man-made form of the IL-1Ra protein, competitively blocks the binding of IL-1β to its receptor to stop inflammation that occurs through the pathway. Anakinra is FDA approved to treat RA and neonatal-onset multisystem inflammatory disease (NOMID). It is sometimes used in less common diseases such as Adult-Onset Still's Disease and Behcet's Disease. Anakinra may have applications for treating lupus nephritis, in which inflammatory reactions caused by anti-dsDNA complexes with extracellular DNA in the glomerular basement membrane cause macrophage IL-1β release onto neighbouring mesangial cell IL-1 receptors.

Inflammatory bowel disease (IBD) includes chronic gastrointestinal disorders characterized by infiltration of inflammatory cells into the mucosa of the digestive tract. Ulcerative colitis (UC) and Crohn's disease (CD) are two prevalent conditions among them.

It has been disclosed that, in certain pre-clinical and clinical studies, certain extracts of *Andrographis paniculata* appear to be useful in treating IBD in humans. The Phase III clinical efficacy of any extracts of *Andrographis paniculata*, however, has yet to be established. A specific extract of *Andrographis paniculata* called HMPL-004 did not meet the desired end points in Phase III clinical trials in the United States.

Disclosed herein are extracts of *Andrographis paniculata* that are highly promising in effectively treating IBD in humans, the preparation method thereof, and the use thereof.

Disclosed herein is an extract of *Andrographis paniculata* comprising at least 50.0% of total andrographolide lactones by weight relative to the weight of the extract, wherein the total andrographolide lactones comprise AND, NAND, DAND, and DDAND, in amounts ranging from 20.0 to 50.0%, 2.0 to 15.0%, 0.5 to 6.0%, and 5.0 to 20.0%, respectively, by weight relative to the weight of the extract.

Also provided is a pharmaceutical composition comprising the extract as disclosed herein and a pharmaceutically acceptable excipient (e.g. a pharmaceutically acceptable carrier).

Also provided is a method of treating autoimmunity and inflammatory diseases in a subject, comprising administering to the subject in need thereof a therapeutically effective amount of the extract or the composition as disclosed herein. The subject described herein can be human.

Also provided is a method of treating inflammatory bowel disease (IBD) in a subject, comprising administering to the subject in need thereof a therapeutically effective amount of the extract or the composition as disclosed herein. The subject described herein can be human.

Also provided is a method of preparing the extract described herein, comprising:
 refluxing the dried aerial part of *Andrographis paniculata* with 80%-95% ethanol; optionally extracting the solid residue with additional 80%-95% ethanol, combining the ethanol phase; collecting the ethanol phase and removing the solvent to provide a first ethanol extract;

adding dextrin to the first ethanol extract; and drying the resulting mixture to obtain a first solid;

extracting the first solid with 90-100% ethanol; collecting the ethanol phase and decolorizing with activated charcoal; collecting the liquid phase and removing the solvent to provide a second solid;

washing the second solid with water; collecting the resulting solid residue; and washing the solid residue obtained after the water-washing step with a weakly polar or non-polar organic solvent; collecting the resulting solid residue to provide the extract of *Andrographis paniculata*.

Also provided is a method of preparing the extract described herein, comprising:

refluxing the dried aerial part of *Andrographis paniculata* with 80%-95% ethanol; optionally extracting the solid residue with additional 80%-95% ethanol, combining the ethanol phase; collecting the ethanol phase and removing the solvent to provide a first ethanol extract;

adding dextrin to the first ethanol extract; and drying the resulting mixture to obtain a first solid;

washing the first solid with water; collecting the resulting solid residue;

extracting the solid residue obtained in the water-washing step with 90-100% ethanol; collecting the ethanol phase and decolorizing with activated charcoal; collecting the liquid phase and removing the solvent to provide a second solid;

washing the second solid with a weakly polar or non-polar organic solvent; collecting the resulting solid residue to provide the extract of *Andrographis paniculata*.

Also provided is a method of enhancing mRNA expression of FGF1 and/or FGF2 comprising contacting the extract of *Andrographis paniculata* as disclosed herein with cells.

BRIEF DESCRIPTION OF DRAWINGS

FIG. 1 shows the effect of Example 1 on LPS induced mRNA expression of pro-inflammatory factors. A. TNFα; B. IL-1β; C. IL-6; D. IL-12p40; E. IL-18; F. Cox-2.

FIG. 2 shows the effect of Example 1 on mRNA expression of pro-inflammatory factors induced by antiCD3 mAb/antiCD28 mAb in human PBMCs. A. CCL-20; B. IFNγ.

FIG. 3 shows the effect of Example 1 on chemokine mRNA expression in T84 cell line. A. CCL-20; B. CXCL-9; C. CXCL-10; D. CXCL-11.

FIG. 4 shows the effect of Example 1 on chemokine mRNA expression in HT29 cell line. A. CCL-20; B. CXCL-10; C. CXCL-11; D. CXCL-16.

FIG. 5 shows the effect of Example 1 on EGF mRNA expression in epithelial cell lines HT29 and T84.

FIG. 6 shows the effect of Example 1 on FGF1 and FGF2 mRNA expression in epithelial cell T84.

FIG. 7 shows the effect of Example 10 on EGF mRNA expression in epithelial cell line HT29.

FIG. 8 shows the effect of Example 10 on FGF1 and FGF2 mRNA expression in epithelial cell T84.

FIG. 9 shows the effect of Example 7 on FGF1 mRNA expression in epithelial cell T84.

DEFINITIONS

As used in the present specification, the following words, phrases, and symbols are generally intended to have the meanings as set forth below, except to the extent that the context in which they are used indicates otherwise. The following abbreviations and terms have the indicated meanings throughout:

As used herein, the term "the weight of the extract" refers to the weight of the extract that does not undergo further drying before next use.

As used herein, the term "total andrographolide lactones" refers to the total of compounds existing in the extract disclosed herein with a diterpenoid-lactone as core structure. For example, the total andrographolide lactones comprises, but not limited to, AND, NAND, DAND, and DDAND.

As used herein, the term "Andrographolide (AND)" refers to the compound having the CAS Registry Number as 5508-58-7.

As used herein, the term "14-deoxyandrographolide (DAND)" refers to the compound having the CAS Registry Number as 4176-97-0.

As used herein, the term "Neoandrographolide (NAND)" refers to the compound having the CAS Registry Number as 27215-14-1.

As used herein, the term "14-Deoxy-11,12-dehydroandrographolide (DDAND)" refers to the compound having the CAS Registry Number as 42895-58-9.

As used herein, the term "80%-95% ethanol" refers to an ethanol containing water (ethanol-water solvent) wherein the amount of ethanol ranges from 80 to 95% by volume relative to the total volume of the ethanol water solvent.

As used herein, the term "90%-100% ethanol" refers to an ethanol containing water (ethanol-water solvent) or no water wherein the amount of ethanol ranges from 90 to 100% by volume relative to the total volume of the ethanol or ethanol-water solvent.

As used herein, the term "absolute ethanol" refers to high-purity ethanol solvent containing at least 99% ethanol, such as ≥99.5% ethanol (industrial grade), ≥99.7% ethanol (chemically pure), ≥99.8% ethanol (analytically pure).

As used herein, the term "subject" means mammals and non-mammals. Mammals means any member of the mamalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a human.

As used herein, the term "pharmaceutically acceptable" means the substance following this term is useful in preparing a pharmaceutical composition and is generally safe, non-toxic, and neither biologically nor otherwise undesirable, especially for human pharmaceutical use.

As use herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the term "weakly polar or non-polar organic solvent" refers to an organic solvent selected from, for example, non-polar solvents, such as alkanes, further such as hexane, petroleum ether, and n-heptane, and from weakly polar solvent such as methyl tert-butyl ether.

Embodiments

Extracts of *Andrographis paniculata*:

Provided is an extract of *Andrographis paniculata* comprising at least 50% of total andrographolide lactones by weight relative to the weight of the extract, wherein the total andrographolide lactones comprise AND, NAND, DAND, and DDAND, in amounts ranging from 20.0 to 50.0%, 2.0 to 15.0%, 0.5 to 6.0%, and 5.0 to 20.0%, respectively, by weight relative to the weight of the extract.

In some embodiments, the extract of *Andrographis paniculata* comprising at least 50% of total andrographolide lactones by weight relative to the weight of the extract, wherein the total andrographolide lactones comprise AND, NAND, DAND, and DDAND, in amounts ranging from 20.0 to 50.0%, 4.0 to 15.0%, 0.5 to 6.0%, and 5.0 to 15.0%, respectively, by weight relative to the weight of the extract.

In some embodiments, the amount of total andrographolide lactones ranges from 55.0 to 75.0% by weight relative to the weight of the extract.

In some embodiments, the amount of total andrographolide lactones ranges from 55.0 to 70.0% by weight relative to the weight of the extract.

In some embodiments, the amount of total andrographolide lactones ranges from 60.0 to 70.0% by weight relative to the weight of the extract.

In some embodiments, the amount of AND ranges from 25.0 to 45.0% by weight relative to the weight of the extract.

In some embodiments, the amount of AND ranges from 25.0 to 30% by weight relative to the weight of the extract.

In some embodiments, the amount of AND ranges from 25.0 to 42.5% by weight relative to the weight of the extract.

In some embodiments, the amount of AND ranges from 30.0 to 45.0% by weight relative to the weight of the extract.

In some embodiments, the amount of NAND ranges from 2.0 to 12.0% by weight relative to the weight of the extract.

In some embodiments, the amount of NAND ranges from 2.0 to 10.0% by weight relative to the weight of the extract.

In some embodiments, the amount of NAND ranges from 2.0 to 9.0% by weight relative to the weight of the extract.

In some embodiments, the amount of NAND ranges from 2.0 to 8.0% by weight relative to the weight of the extract.

In some embodiments, the amount of NAND ranges from 2.0 to 6.0% by weight relative to the weight of the extract.

In some embodiments, the amount of NAND ranges from 2.0 to 4.0% by weight relative to the weight of the extract.

In some embodiments, the amount of NAND ranges from 4.0 to 12.0% by weight relative to the weight of the extract.

In some embodiments, the amount of NAND ranges from 6.0 to 10.0% by weight relative to the weight of the extract.

In some embodiments, the amount of NAND ranges from 6.0 to 9.0% by weight relative to the weight of the extract.

In some embodiments, the amount of NAND ranges from 6.0 to 8.0% by weight relative to the weight of the extract.

In some embodiments, the amount of DAND ranges from 1.0 to 5.0% by weight relative to the weight of the extract.

In some embodiments, the amount of DAND ranges from 1.0 to 4.0% by weight relative to the weight of the extract.

In some embodiments, the amount of DAND ranges from 2.0 to 4.0% by weight relative to the weight of the extract.

In some embodiments, the amount of DDAND ranges from 5.0 to 15.0% by weight relative to the weight of the extract.

In some embodiments, the amount of DDAND ranges from 10.0 to 15.0% by weight relative to the weight of the extract.

In some embodiments, the amount of DDAND ranges from 5.0 to 10.0% by weight relative to the weight of the extract.

In some embodiments, the amount of DDAND ranges from 6.0 to 9.0% by weight relative to the weight of the extract.

In some embodiments, the amount of DDAND ranges from 7.0 to 9.0% by weight relative to the weight of the extract.

Methods for Preparation:

Method 1:

Further provided is a first method of preparing the extract of *Andrographis paniculata*, comprising:

refluxing the dried aerial part of *Andrographis paniculata* with 80%-95% ethanol; optionally extracting the solid residue with additional 80%-95% ethanol, combining the ethanol phase; collecting the ethanol phase and removing the solvent to provide a first ethanol extract;

adding dextrin to the first ethanol extract; and drying the resulting mixture to obtain a first solid;

extracting the first solid with 90-100% ethanol; collecting the ethanol phase and decolorizing with activated charcoal; collecting the liquid phase and removing the solvent to provide a second solid;

washing the second solid with water; collecting the resulting solid residue; and washing the solid residue obtained after the water-washing step with a weakly polar or non-polar organic solvent; collecting the resulting solid residue to provide the extract of *Andrographis paniculata*.

In some embodiments, the dried aerial part of *Andrographis paniculata* was crushed before being subject to extraction with 80-95% ethanol.

In some embodiments, the 80-95% ethanol used in the first step is 89-91% ethanol.

In some embodiments, the 80-95% ethanol used in the first step is 90% ethanol.

In some embodiments, the refluxing of the dried aerial part of *Andrographis paniculata* with 80-95% ethanol is performed twice (i.e., extracting the solid residue with additional 80%-95% ethanol once), each time for about 2 hours, i.e., 96 to 144 minutes, such as 110 to 130 minutes. In some embodiments, the optional extraction of the solid residue with additional 80%-95% ethanol is performed by refluxing the residue solids with additional 80%-95% ethanol for about 2 hours, i.e., 96 to 144 minutes, such as 110 to 130 minutes.

In some embodiments, the ratio of the dried aerial part of *Andrographis paniculata* to 80-95% ethanol (or to the additional 80-95% ethanol) (kg/L) ranges from 1:4 to 1:10, such as from 1:5 to 1:6.

In some embodiments, the first ethanol extract has a density of 1.0-1.1 g/ml.

In some embodiments, the amount of dextrin added is about 3% (i.e., 2.4 to 3.6%) by weight of the dried aerial part of *Andrographis paniculata* used. In some embodiments, dextrin was added in the form of a solution, such as in the form of water solution.

In some embodiments, the extraction of the first solid with 90-100% ethanol is performed 1-2 times, such as 2 times, each time for about 1 hour, i.e., 48 to 72 minutes, such as 55 to 65 minutes.

In some embodiments, the 90-100% ethanol used in the third step is absolute ethanol.

In some embodiments, the 90-100% ethanol used in the third step is 95% ethanol.

In some embodiments, the extraction of the first solid with 90-100% ethanol can utilize any one of the following extraction processes: (1) stirring at room temperature, (2) stirring while heating at 30-80° C., or (3) a refluxing extraction process. In some embodiments, the extraction with 90-100% ethanol refers to a refluxing extraction process, i.e., refluxing in 90-100% ethanol, such as refluxing in absolute ethanol.

In some embodiments, the amount of activated charcoal used is 5-20%, such as 20%, by weight, of the first solid obtained after dextrin addition.

In some embodiments, the decolorization with activated charcoal was performed at 50-80° C., such as 58-63° C., for an appropriate time as recognized by one of ordinary skill in the art.

In some embodiments, the water-washing step refers to stirring in water at 70-90° C., such as 80-85° C., for an appropriate time as recognized by one of ordinary skill in the art. In some embodiments, the ratio of the first solid obtained after dextrin addition to the water (kg/L) ranges from 1:5 to 1:15, such as from 1:8-1:12, or 1:10.

In some embodiments, the water-washing step is performed one or more times, such as once or twice.

In some embodiments, the weakly polar or non-polar organic solvent can be selected from, for example, non-polar solvents, such as alkanes, further such as hexane, petroleum ether, and n-heptane, and from weakly polar solvent such as methyl tert-butyl ether. In some embodiments, the weakly polar or non-polar organic solvent is n-heptane.

In some embodiments, prior to the step of washing with weakly polar or non-polar organic solvent, the solid residue obtained in the water-washing step is dissolved in absolute ethanol and concentrated to afford a solid.

In some embodiments, the step of washing with weakly polar or non-polar organic solvent is performed at 15-30° C., such as 20-30° C., for an appropriate time as recognized by one of ordinary skill in the art. In some embodiments, the step of washing with weakly polar or non-polar organic solvent refers to stirring in the weakly polar or non-polar organic solvent at 15-30° C., such as 20-30° C., for an appropriate time as recognized by one of ordinary skill in the art.

Method 2:

Further provided is a second method of preparing the extract of *Andrographis paniculata*, as disclosed herein, comprising:

refluxing the dried aerial part of *Andrographis paniculata* with 80%-95% ethanol; optionally extracting the solid residue with additional 80%-95% ethanol, combining the ethanol phase; collecting the ethanol phase and removing the solvent to provide a first ethanol extract;

adding dextrin to the first ethanol extract; and drying the resulting mixture to obtain a first solid;

washing the first solid with water; collecting the resulting solid residue;

extracting the solid residue obtained in the water-washing step with 90-100% ethanol; collecting the ethanol phase and decolorizing with activated charcoal; collecting the liquid phase and removing the solvent to provide a second solid;

washing the second solid with a weakly polar or non-polar organic solvent; collecting the resulting solid residue to provide the extract of *Andrographis paniculata*.

In some embodiments, the dried aerial part of *Andrographis paniculata* was crushed before being subject to extraction with 80-95% ethanol.

In some embodiments, the 80-95% ethanol used in the first step is 89-91% ethanol.

In some embodiments, the 80-95% ethanol used in the first step is 90% ethanol.

In some embodiments, the refluxing of the dried aerial part of *Andrographis paniculata* with 80-95% ethanol is performed twice (i.e., extracting the solid residue with additional 80%-95% ethanol once), each time for about 2 hours, i.e., 96 to 144 minutes, such as 110 to 130 minutes.

In some embodiments, the optional extraction of the solid residue with additional 80%-95% ethanol is performed by refluxing the residue solids with additional 80%-95% ethanol for about two hours, i.e., 96 to 144 minutes, such as 110 to 130 minutes.

In some embodiments, the ratio of the dried aerial part of *Andrographis paniculata* to 80-95% ethanol (or to the additional 80-95% ethanol) (kg/L) ranges from 1:5 to 1:10, such as from 1:5 to 1:6.

In some embodiments, the first ethanol extract has a density of 1.0-1.1 g/ml.

In some embodiments, the amount of dextrin added is about 3% (i.e., 2.4 to 3.6%) by weight of the dried aerial part of *Andrographis paniculata* used. In some embodiments, dextrin was added in the form of a solution, such as in the form of water solution.

In some embodiments, the water-washing step refers to stirring in water at 70-90° C., such as 80-85° C. In some embodiments, the ratio of the first solid obtained after dextrin addition to the water (kg/L) ranges from 1:5 to 1:15, such as from 1:8-1:12, or 1:10.

In some embodiments, the water-washing step is performed one or more times, such as once or twice, for an appropriate time as recognized by one of ordinary skill in the art.

In some embodiments, the extraction with 90-100% ethanol is performed 1-2 times, such as twice, each time for about 1 hour, i.e., 48 minutes to 72 minutes, such as 55 to 65 minutes.

In some embodiments, the 90-100% ethanol used in the fourth step is absolute ethanol.

In some embodiments, the 90-100% ethanol used in the fourth step is 95% ethanol.

In some embodiments, the extraction with 90-100% ethanol can be any one of the following extraction processes: (1) stirring at room temperature, (2) stirring while heating at 30-80° C., or (3) a refluxing extraction process. In some embodiments, the extraction with absolute ethanol refers to a refluxing extraction process, i.e., refluxing in 90-100% ethanol, such as refluxing in absolute ethanol.

In some embodiments, the amount of activated charcoal used is 5-20%, such as 20%, by weight, of the first solid obtained after dextrin addition.

In some embodiments, the decolorization with activated charcoal was performed at 50-80° C., such as 70-80° C., for an appropriate time as recognized by one of ordinary skill in the art.

In some embodiments, the weakly polar or non-polar organic solvent can be selected from, for example, non-polar solvents, such as alkanes, further such as hexane, petroleum ether, and n-heptane, and from weakly polar solvent such as methyl tert-butyl ether. In some embodiments, the weakly polar or non-polar organic solvent is n-heptane.

In some embodiments, the step of washing with weakly polar or non-polar organic solvent is performed at 15-30° C., such as 20-30° C., for an appropriate time as recognized by one of ordinary skill in the art. In some embodiments, the step of washing with weakly polar or non-polar organic solvent refers to stirring in the weakly polar or non-polar organic solvent at 15-30° C., such as 20-30° C., for an appropriate time as recognized by one of ordinary skill in the art.

Use of the Extracts Disclosed Herein

Further disclosed is a method of treating autoimmunity and inflammatory diseases in a subject, comprising administering to the subject in need thereof a therapeutically effective amount of the extract as disclosed herein.

Further disclosed is a use of the extract as disclosed herein for treating autoimmunity and inflammatory diseases in a subject.

Further disclosed is a use of the extract as disclosed herein in the manufacture of a medicament for treating autoimmunity and inflammatory diseases in a subject.

In some embodiment, the autoimmunity and inflammatory diseases is selected from rheumatoid arthritis (RA), inflammatory bowel disease (IBD), psoriasis, systemic lupus erythematosus (SLE), asthma, and chronic obstructive pulmonary disease (COPD).

In some embodiment, the inflammatory bowel disease is Crohn's disease (CD).

In some embodiments, the inflammatory bowel disease is ulcerative colitis (UC).

In some embodiments, the extract is in the form a pharmaceutically acceptable composition comprising the extract as disclosed herein.

In some embodiments, the expression level of FGF1 and/or FGF2 in the subject is elevated after administering to the subject the therapeutically effective amount of the extract as disclosed herein.

Composition

Further disclosed is a pharmaceutical composition comprising the extract as disclosed herein and a pharmaceutically acceptable excipient (e.g. a pharmaceutically acceptable carrier).

The pharmaceutical composition comprising the extract disclosed herein, and a pharmaceutically acceptable excipient, can be administered orally in solid dosage forms, such as capsules and tablets.

Gelatin capsules containing the extract and powdered excipients, such as lactose, starch, cellulose derivatives, magnesium stearate, stearic acid, silicon dioxide and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract. For example, the tablets can be film-coated with a paste prepared by mixing excipients comprising hypromellose, propylene glycol, titanium dioxide, and purified water.

A pharmaceutically acceptable excipient is, for example, selected from excipients that are compatible with the extract disclosed herein and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the extracts disclosed herein. Examples of other excipients include colloidal silicon dioxide, magnesium stearate, cellulose, sodium lauryl sulfate, and pigments such as D&C Yellow #10. Suitable pharmaceutically acceptable excipients are disclosed in Remington's Pharmaceutical Sciences, A. Osol, a standard reference text in the art.

Useful pharmaceutical dosage forms for administration of the extract disclosed herein include, but are not limited to, hard and soft gelatin capsules, and tablets.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 10,000, such as from 0.1 to 2000 milligrams per day. For example, 10-500 milligrams once or multiple times per day may be effective to obtain the desired results.

In some embodiments, the extract disclosed herein can be present in an amount of 1, 5, 10, 15, 20, 25, 50, 75, 80, 85, 90, 95, 100, 125, 150, 200, 250, 300, 400 or 500 mg in a tablet or capsule.

Analytical Methods 1. qHNMR (Quantitative HNMR) Method for Determination the Amount of the Total Andrographolide Lactones in the Extracts:

The amount of the total andrographolide lactones in the extracts was analyzed via qHNMR method detecting three typical types (namely as type A, type B, and type C) of diterpenoid lactones. For example, AND belongs to type A, DAND and NAND belong to type B, and DDAND belongs to type C.

1.1 Instruments and Parameters:

NMR: Varian 400-MR or equivalent;
Probe: Varian 400 ASW PFG
Data acquisition and processing system: VNMRJ 4.0
Pulse sequence: s2pul
Temperature: 20-30° C.
Spectral width: 6378 Hz
Delay time: 12 s
Pulse width: 10 degree
Acquisition time: 2.569 s
Number of Scans: 32

1.2 Reagents

Deuterated reagent: DMSO-d6 (containing tetramethylsilane, TMS), J&K
Internal standard: 2,3,5-Triiodobenzoic acid (TIBZ), Amethyst
Reference substance:
AND, Guilin Sanleng Biotech Co. Ltd
DAND, In-house production
DDAND, In-house production 1.3 Preparation of Sample Solution Sample of the extract (75±5 mg) and TIBZ (21±2 mg) were accurately weighed and added into a 5 ml centrifuge tube. Then, DMSO-d6 (1 ml) was added. Shake and sonicate for at least 20 min until the sample was dissolved completely, and then allow to reach room temperature. Transfer 0.5 ml of the solution into an NMR tube.

1.4 Sample Measurement 1.4.1 Calibration and Integration a. The chemical shift of TMS was set as 0 ppm. Perform manual integral method.
b. The integral interval of TIBZ was 8.246 to 8.360 ppm. When the TIBZ peak shifted, the integral interval can be appropriately adjusted, with integral width keeping unchanged, to let the TIBZ peak locate in the middle of the integral interval.
c. The integral interval of type A of the diterpenoid lactones was 6.578-6.670 ppm.
d. The integral interval of type B of the diterpenoid lactones was 7.430-7.490 ppm.

e. The integral interval of type C of the diterpenoid lactones was 7.610-7.680 ppm.
f. The peak area of TIBZ was set as 1000.

1.4.2 Results and Calculation

The content of type A of the diterpenoid lactones ($X_A$ %) was calculated according to the following equation:

$$X_A\% = \frac{As \times Mr \times Pr \times Ws}{Ar \times Wr \times Ms} \times 100\%$$

wherein,
As is the peak area of type A of the diterpenoid lactones
Ar is the peak area of TIBZ
Mr is the weight of TIBZ, mg
Pr is the purity of TIBZ, %
Wr is the molecule weight of TIBZ
Ms is the weight of the sample
Ws is the molecule weight of AND Similarly, the contents of type B and C of the diterpenoid lactones ($X_B$ % and $X_C$ %) were calculated as above.

The content of the total andrapholide lactones in the sample ($X_{sum}$ %) was calculated as follows:

$$X_{sum}\% = X_A\% + X_B\% + X_C\%.$$

2. HPLC Method for Determination of AND, NAND, DAND, and DDAND 2.1 Instruments and Parameters:

Chromatographic system: Waters Alliance™ 2695 HPLC, or equivalent
Column: Agilent Zorbax Extend C18, 3.5 um, 150 mm×4.6 mm (PN:763953-902)
Detector: 2487 dual wavelength detector
Detection wavelength: 220 nm
Mobile phase:
Phase A: water
Phase B: acetonitrile
Gradient table:

| Time | % A | % B |
|------|-----|-----|
| 0 | 90 | 10 |
| 5 | 82 | 18 |
| 23 | 81 | 19 |
| 26 | 72 | 28 |
| 47 | 69 | 31 |
| 49 | 10 | 90 |
| 53 | 10 | 90 |
| 55 | 90 | 10 |
| 60 | 90 | 10 |

Flow rate: 1.0 ml/min
Column temperature: 35° C.
Injection volume: 10 ul
Elution time: 60 min 2.2 Preparation of Reference Solution:

2.2.1 Diluent

Methanol.

2.2.2 Preparation of Stock Solution

DAND (50±1 mg) was accurately weighed and added into a 50 ml volumetric flask (Flask I). Then, diluent (about 40 ml) was added. Shaking and sonicating Flask I for at least 10 min until DAND was dissolved completely. After allowing to reach room temperature, diluted to desired volume with the diluent.

AND (75±1 mg), NAND (25±1 mg), and DDAND (25±1 mg) were accurately weighed and added into a 50 ml volumetric flask (Flask II). The solution (5 ml) prepared in Flask I was accurately pipetted into Flask II. Then, diluent (about 35 ml) was added. Shaking and sonicating for at least 15 min until the solids were dissolved completely. After allowing to reach room temperature, diluted to desired volume with the diluent.

2.2.3 Preparation of Working Standard Solution

The stock solution (10 ml) was accurately pipetted into a 50 ml volumetric flask, which was subsequently diluted to desired volume with the diluent.

2.3 Preparation of Sample Solution

The extract sample (100±1 mg) was accurately weighed and added to a 100 ml volumetric flask. Diluent (about 80 ml) was added. Shaking and sonicating for at least 15 min until the sample was dissolved completely. After allowing to reach room temperature, diluted to desired volume with the diluent.

2.4 Results and Calculation

The content of AND in the sample (X %) was calculated according to the following equation:

$$X\% = \frac{A_{spl} \times C_s \times D}{A_s \times W} \times 100\%$$

wherein,
X %: The content of AND in the sample
$A_{spl}$: Absorption value of AND in the sample
$A_s$: Absorption value of AND in working standard solution
$C_s$: Concentration of AND in working standard solution, mg/ml
D: Sample dilution factor, 100
W: Weight of the sample, mg Similarly, the contents of NAND, DAND, and DDAND in the sample can be calculated as above.

EXAMPLES

The examples below are intended to be purely exemplary and should not be considered to be limiting in any way. Efforts have been made to ensure accuracy with respect to numbers used (for example, amount, temperature, etc.) but some experimental errors and deviations should be accounted for. Unless indicated otherwise, parts are parts by weight, temperature is in degrees Centigrade.

Example 1

Preparation of the Extract of *Andrographis paniculata*

The dried aerial part of *Andrographis paniculata* (300 kg) was extracted with 89-91% ethanol (1800 L) by refluxing for 2 hours. The ethanol phase was collected and 89-91% ethanol (1500 L) was added to the residue, which was followed by refluxing for 2 hours again. The ethanol solutions were sieved through an 80 mesh screen and combined, and then was concentrated under reduced pressure (temperature: ≤65° C., pressure: −0.045~−0.100 MPa) and sieved through a 40 mesh screen to afford a wet mixture having a density of 1.022 g/ml. Dextrin (9 kg, available from Roquette, France, Product Code: TACKIDEX B167) was dissolved in water (143.96 L) and then was added to the wet mixture, which was then spray-dried (inlet: 185-195° C.; outlet: 95-115° C.) to give 26.45 kg solid powder.

The solid powder (120 g of the 26.45 kg obtained in the above step) was added to absolute ethanol (1.2 L). The mixture was stirred at 70-75° C. for 1 hour, which was followed by immediate filtration. Activated charcoal (24 g) was added to the filtrate. The resulting mixture was stirred for 1 hour at 60° C., followed by immediate filtration. The ethanol filtrate was concentrated to afford 59.5 g solid.

The solid (52 g of the 59.5 g obtained in the above step) was added to 520 mL $H_2O$. The resulting mixture was stirred for 1 h at 80° C. and filtered. The filter cake was dissolved in absolute ethanol and concentrated to afford 19.2 g solid.

The solid (19 g of the 19.2 g obtained in the above step) was added to 570 mL n-heptane. The resulting mixture was stirred for 24 h at room temperature and filtered. The filter cake was dried to give 17 g extract of *Andrographis paniculata*.

The components of the extract were identified by the analytical methods as described above. The results are shown in Table 1 below.

Example 2

Preparation of the Extract of *Andrographis paniculata*

The dried aerial part of *Andrographis paniculata* (300 kg) was extracted with 89-91% ethanol (1800 L) by refluxing for 2 hours. The ethanol phase was collected and 89-91% ethanol (1500 L) was added to the residue, which was followed by refluxing for 2 hours again. The ethanol solutions were sieved through an 80 mesh screen and combined, and then was concentrated under reduced pressure (temperature: ≤65° C., pressure: −0.045~−0.100 MPa) and sieved through a 40 mesh screen to afford a wet mixture having a density of 1.005 g/ml. Dextrin (9 kg) was dissolved in water (134.29 L) and then was added to the wet mixture, which was then spray-dried (inlet: 185-195° C.; outlet: 95-115° C.) to give 33.44 kg solid powder The solid powder (1.615 kg of the 33.44 kg obtained in the above step) was added to absolute ethanol (16.15 L). The mixture was stirred at 70~75° C. for 1 hour, which was followed by immediate filtration. Activated charcoal (323 g) was added to the filtrate. The resulting mixture was stirred for 1 hour at 60° C. and followed by immediate filtration. The ethanol solution was concentrated to afford 805.8 g solid.

The solid (781.3 g of the 805.8 g obtained in the above step) was added to water (7.8 L). The resulting mixture was stirred for 1 h at 80~85° C. and filtered. The filter cake was dissolved in absolute ethanol and concentrated to afford 318.2 g solid.

The solid (278.8 g of the 318.2 g obtained in the above step) was added to n-heptane (8.4 L). The resulting mixture was stirred for 24 h at 23-25° C. and filtered. The filter cake was dried to give 252.8 g extract of *Andrographis paniculata*.

The components of the extract were identified by the analytical methods as describe above. The results are shown in Table 1 below.

Example 3

Preparation of the Extract of *Andrographis paniculata*

The dried aerial part of *Andrographis paniculata* (300 kg) was extracted with 89-91% ethanol (1800 L) by refluxing for 2 hours. The ethanol phase was collected, and 89-91% ethanol (1500 L) was added to the residue, which was followed by refluxing for 2 hours again. The ethanol solutions were sieved through an 80 mesh screen and combined, and then was concentrated under reduced pressure (temperature: ≤65° C., pressure: −0.045~−0.100 MPa) and sieved through a 40 mesh screen to afford a wet mixture having a density of 1.005 g/ml. Dextrin (9 kg) was dissolved in water (134.29 L) and then was added to the wet mixture, which was then spray-dried (inlet: 185-195° C.; outlet: 95-115° C.) to give 33.44 kg solid powder.

The solid powder (200.01 g of the 33.44 kg obtained in the above step) was added to water (2 L) and stirred at 80-82° C. for 1 hour. After standing at 80-82° C. for 40 min, the supernatant liquid was discarded, and the solid residue was added to water (2 L) following by stirring at 80-82° C. for 1 hour. The resulting mixture was placed at 80-82° C. for a further 60 min. The supernatant liquid was dumped, and the solid residue was added to absolute ethanol (2 L). The mixture was stirred and heating at 75-77° C. for 1 hour, followed by immediate filtration.

Activated charcoal (40.0 g) was added to the filtrate obtained in the previous step. The resulting mixture was stirred for 1 hour at 75-77° C. followed by immediate filtration. The filtrate was concentrated, which was subsequently grinded and sieved through 60 mesh screen to afford 34.27 g solid.

The solid (30.0 g of the 34.27 g obtained in the above step) was added to n-heptane (0.9 L). The resulting mixture was stirred for 3 h at 25-26° C. and followed by immediate filtration. The filter cake was dried, grinded, and sieved through 60 mesh screen to give 29.25 g extract of *Andrographis paniculata*.

The components of the extract were identified by the analytical methods as describe above. The results are shown in Table 1 below.

Example 4

Preparation of the Extract of *Andrographis paniculata*

The dried aerial part of *Andrographis paniculata* (300 kg) was extracted with 89-91% ethanol (1800 L) by refluxing for 2 hours. The ethanol phase was collected and 89-91% ethanol (1500 L) was added to the residue, which was followed by refluxing for 2 hours again. The ethanol solutions were sieved through an 80 mesh screen and combined, and then was concentrated under reduced pressure (temperature: ≤65° C., pressure: −0.045~−0.100 MPa) and sieved through a 40 mesh screen to afford a wet mixture having a density of 1.002 g/ml. Dextrin (9 kg) was dissolved in water (143.88 L) and then was added to the wet mixture, which was then spray-dried (inlet: 185-195° C.; outlet: 95-115° C.) to give 27.10 kg solid powder.

The solid powder (4 kg of the 27.10 kg obtained in the above step) was added to water (40 L) and stirred for 1 hour (inner temperature 80° C.). After standing at 88° C. (inner temperature 80° C.) for 80 min, the supernatant liquid was removed out. Water (40 L) was added and stirred for 1 hour (inner temperature 80° C.). After standing at 88° C. (inner temperature 80° C.) for further 60 min, the supernatant liquid was removed out. Absolute ethanol (40 L) was added and stirred at 82-85° C. (inner temperature 75-76° C.) for 1 hour.

And then activated charcoal (0.8 kg) was added and stirred for 1 hour at 82° C. (inner temperature 75-76° C.), followed by immediate filtration. The filtrate was concentrated to dryness, which was subsequently grinded and sieved through a 60 mesh screen to afford 710 g solid.

The solid (700 g of 710 g obtained in the above step) was added to n-heptane (210 L). The resulting mixture was stirred for 3 h at room temperature (inner temperature 26-27° C.), followed by immediate filtration. The filter cake was dried, grinded, and sieved through a 60 mesh screen to give 653.1 g extract of *Andrographis paniculata*.

The components of the extract were identified by the analytical methods as describe above. The results are shown in Table 1 below.

Examples 5-11

Preparation of the Extract of *Andrographis paniculata*

Similarly, Examples 5-11 of the extract of *Andrographis paniculata* disclosed herein were obtained according to the procedure as described in Example 4. The components of the extract were identified by the analytical methods as described above. The results are shown in Table 1 below.

TABLE 1

The content of 4 single compounds, total andrographolide lactones in the extract from *Andrographis paniculata*

| Examples | AND (%) | NAND (%) | DAND (%) | DDAND (%) | Total andrographolide Lactones (%) |
|---|---|---|---|---|---|
| Example 1 | 26.7% | 8.2% | 1.8% | 6.6% | 56.8% |
| Example 2 | 28.4% | 7.4% | 2.0% | 6.9% | 56.7% |
| Example 3 | 37.5% | 7.1% | 2.3% | 8.0% | 62.29% |
| Example 4 | 38.3% | 6.7% | 2.2% | 7.8% | 61.40% |
| Example 5 | 39.9% | 7.1% | 2.2% | 8.2% | 64.04% |
| Example 6 | 37.0% | 6.6% | 2.1% | 7.7% | 60.01% |
| Example 7 | 38.3% | 6.7% | 3.2% | 9.5% | |
| Example 8 | 35.1% | 3.2% | 1.8% | 14.5% | 62.7% |
| Example 9 | 33.5% | 4.7% | 4.2% | 12.2% | 62.9% |
| Example 10 | 36.6% | 6.7% | 2.1% | 7.7% | 61.3% |
| Example 11 | 41.1% | 7.1% | 2.2% | 8.5% | 67.9% |

The following embodiments are also within the scope of this disclosure

1. An extract of *Andrographis paniculata* comprising at least 50% of total andrographolide lactones by weight relative to the weight of the extract, wherein the andrographolide lactones comprise AND, NAND, DAND, and DDAND, with amount ranging from 20.0 to 50.0%, 2.0 to 15.0%, 0.5 to 6.0%, and 5.0 to 20.0%, respectively, by weight relative to the weight of the extract.

2. The extract of embodiment 1, wherein the extract of *Andrographis paniculata* comprising at least 50% of total andrographolide lactones by weight relative to the weight of the extract, wherein the andrographolide lactones comprise AND, NAND, DAND, and DDAND, with amount ranging from 20.0 to 50.0%, 4.0 to 15.0%, 0.5 to 6.0%, and 5.0 to 15.0%, respectively, by weight relative to the weight of the extract.

3. The extract of embodiment 1, wherein the amount of total andrographolide lactones ranges from 55.0 to 75.0% by weight relative to the weight of the extract.

4. The extract of any one of embodiment 1-3, wherein the amount of total andrographolide lactones ranges from 55.0 to 70.0% by weight relative to the weight of the extract.

5. The extract of any one of embodiment 4, wherein the amount of total andrographolide lactones ranges from 60.0 to 70.0% by weight relative to the weight of the extract.

6. The extract of any one of embodiments 1-5, wherein the amount of AND ranges from 25.0 to 45.0% by weight relative to the weight of the extract.

7. The extract of any one of embodiment 6, wherein the amount of AND ranges from 25.0 to 30.0% by weight relative to the weight of the extract 8. The extract of any one of embodiment 6, wherein the amount of AND ranges from 30.0 to 45.0% by weight relative to the weight of the extract.

9. The extract of any one of embodiments 1-8, wherein amount of NAND ranges from 2.0 to 12.0% by weight relative to the weight of the extract.

10. The extract of any one of embodiment 9, the amount of NAND ranges from 2.0 to 10.0% by weight relative to the weight of the extract.

11. The extract of any one of embodiment 10, the amount of NAND ranges from 2.0 to 9.0% by weight relative to the weight of the extract.

12. The extract of any one of embodiment 11, the amount of NAND ranges from 2.0 to 8.0% by weight relative to the weight of the extract.

13. The extract of any one of embodiment 12, the amount of NAND ranges from 2.0 to 6.0% by weight relative to the weight of the extract.

14. The extract of any one of embodiment 13, the amount of NAND ranges from 2.0 to 4.0% by weight relative to the weight of the extract.

15. The extract of any one of embodiments 1-8, wherein the amount of NAND ranges from 4.0 to 12.0% by weight relative to the weight of the extract.

16. The extract of any one of embodiment 15, wherein the amount of NAND ranges from 6.0 to 10.0% by weight relative to the weight of the extract.

17. The extract of any one of embodiment 16, wherein the amount of NAND ranges from 6.0 to 9.0% by weight relative to the weight of the extract.

18. The extract of any one of embodiments 1-17, wherein the amount of DAND ranges from 1.0 to 5.0% by weight relative to the weight of the extract.

19. The extract of any one of embodiment 18, wherein the amount of DAND ranges from 1.0 to 4.0% by weight relative to the weight of the extract.

20. The extract of any one of embodiments 1-19, the amount of DDAND ranges from 5.0 to 15.0% by weight relative to the weight of the extract.

21. The extract of any one of embodiments 1-19, the amount of DDAND ranges from 10.0 to 15.0% by weight relative to the weight of the extract.

22. The extract of any one of embodiment9 20, wherein the amount of DDAND ranges from 5.0 to 10.0% by weight relative to the weight of the extract.

23. The extract of any one of embodiment 22, wherein the amount of DDAND ranges from 6.0 to 9.0% by weight relative to the weight of the extract.

24. A pharmaceutical composition comprising an extract of any one of embodiments 1-23 and a pharmaceutically acceptable excipient.

25. A method of treating inflammatory bowel disease (IBD) in a subject, comprising administering to the subject in need thereof a therapeutically effective amount of a pharmaceutical composition of embodiment 24.

26. The method of embodiment 25, wherein the inflammatory bowel disease (IBD) is Crohn's disease or ulcerative colitis.

In Vitro Bioassay

Assay 1: Inhibition of IL-1β Expression

Lamna propria dendritic cells and macrophages are key antigen-presenting cells that are found in the inflamed mucosa in patients with IBD. Upon activation, which occurs in response to components of the commensal microbiota and Toll-like receptor signaling, these cells produce large amounts of pro-inflammatory cytokines, such as IL-1β, etc. A significantly increased level of IL-1β was found in the intestinal mucosa of the patients with CD and UC when compared with healthy subjects, indicating an increased activation of the IL-1β in the disease. A great amount of evidence suggested that IL-1β has a prominent role in the initiation of colonic inflammation. The inhibition of IL-1β has been linked to effective therapeutic treatment of IBD, such as CD and UC. [Neurath M F. Cytokines in inflammatory bowel disease. Nat Rev Immunol. 2014 May; 14(5): 329-42]

Human THP-1 monocytic cells induced by LPS, a chemical from outer membrane of Gram-negative bacteria, were utilized to evaluate inhibitory activity of the samples disclosed herein and *Andrographis paniculata* extract Standard 1 in vitro. Standard 1 is within the scope of disclosure of WO 2009/059158, and was prepared using the extract preparation method disclosed in WO2009/059158.

THP-1 cells (obtained from ATCC, Cat.: TIB-202) were maintained at 37° C. with 5% $CO_2$ in 75 $cm^2$ flask (Corning, Cat.: 430641) with about 20 mL culture medium (RPMI-1640 with 10% heat-inactivated FBS and 0.1% 55 mM 2-mercaptoethanol and 1% GlutaMAX). The cells were sub-cultured to $2\times10^5$ cells/mL every 3 days or $3\times10^5$ cells/mL every 2 days. For the assay, the THP-1 cell suspension was collected and centrifuged at 1000 rpm for 5 min. The supernatant was removed and discarded. The cells were resuspended in fresh medium. The cell density was determined and adjusted to the density of $6\times10^5$ cells/mL. The cells were seeded into a 96-well plate (BD falcon, Cat.: 353072) and incubated at 37° C. with 5% $CO_2$ until test samples treatment.

Two examples of *Andrographis paniculata* extracts were serially diluted in DMSO and further diluted in medium. One of the two examples was within the scope of disclosure of WO 2009/059158 and was used as a standard 1. The other example was within the scope of the extract disclosed herein ("Example 1"). Series diluted solution was added into wells. The final concentrations for each of Standard 1 and Example 1 were: 300, 120, 48, 19.2, 7.68, 3.07, 1.23, 0.49, 0.20 and 0.08 μg/mL. The plate was incubated for 30 minutes until stimuli LPS/PMA treatment. A combination of LPS and PMA was added into wells. The final concentrations of stimuli were 1 μg/mL LPS plus 10 ng/mL PMA. Then, the plate was incubated at 37° C. with 5% $CO_2$ for about 18 hours. The ELISA plate was also coated by adding 100 μL capture antibody working solution into each well following the kit instruction. The ELISA plate was incubated at room temperature overnight.

On the second day, the cell culture plate was centrifuged at 900 rpm for 10 minutes. 120 μL/well supernatants were transferred into a fresh 96-well plate. The IL-1β production in supernatants was measured by using commercial IL-1β ELISA Kit (R&D systems, Cat. DY201). Finally, the OD value for each well was measured by a spectrophotometer. The concentration (C) of IL-1 β for each sample was determined by the blank-corrected average OD value and the IL-1 β standard curve. The inhibition ratio was calculated as follows:

$$\text{Inhibition Ratio (\%)} = \frac{C_{LPS/PMA} - C_{test\,sample}}{C_{LPS/PMA}} \times 100$$

where $C_{test\,sample}$ is the IL-1β concentration of cells treated with the test samples and stimuli LPS/PMA, $C_{LPS/PMA}$ is the IL-1β concentration of cells treated with stimuli LPS/PMA only. $IC_{50}$ was calculated using 4PL model by fitting bottom value to 0 and top value to 100. The final result was expressed as relative potency by comparing Example 1 with Standard 1. The relative potency was calculated as follows:

$$\text{Relative potency}(\%) \times = \frac{IC_{50\,Standard\,1}}{IC_{50\,Example\,1}} \times 100$$

Similarly, other *Andrographis paniculata* extracts as disclosed herein ("Examples 2-6") were tested. The results showed that Examples 1-6 were much more potent than Standard 1 with the relative potency of 419.2% (Mean) (n=6). The results are shown in Table 2 below.

TABLE 2

Inhibitory potency on LPS/PMA induced IL-1β production in THP-1 cells

| Example # | $IC_{50}$ (μg/mL) | IL-1β production relative potency % based on Standard 1 |
|---|---|---|
| 1 | 1.8 | 296.0% |
| 2 | 2.1 | 343.2% |
| 3 | 1.7 | 521.9% |
| 4 | 0.9 | 478.5% |
| 5 | 1.2 | 482.0% |
| 6 | 0.9 | 393.3% |

Assay 2: Inhibition of NF-κB Activation

Dysregulated cytokine production and signaling mechanisms by intestinal epithelial cells, lymphocytes and macrophages have been implicated in the pathogenesis of IBD, and the transcription factor NF-κB is one of the major regulatory components in this complex system. The expression and activation of NF-κB is strongly induced in the inflamed gut of IBD patients, especially in macrophages and epithelial cells, where augmented levels of NF-κB correlated significantly with the severity of intestinal inflammation. In IBD patients, higher NF-κB expression in mucosal macrophages is accompanied by an increased capacity to produce and secrete pro-inflammatory cytokines, such as TNF-α, IL-1, IL-6, IL-12 and IL-23, etc., resulting in the perpetuation of mucosal inflammation and tissue damage. Blockade of NF-κB activation has become a therapeutic strategy in IBD. For instance, corticosteroids are able to inhibit NF-κB activation. Consistent with that, colonic mononuclear-, epithelial- and endothelial cells from glucocorticoid-treated IBD patients showed significantly lower NF-κB activation than cells from untreated patients. [Atreya I., et al. NF-κB in inflammatory bowel disease. J Intern Med. 2008 June; 263(6):591-6]

Inhibitory potencies of the samples disclosed herein and Standard 1 were simultaneously evaluated in TNF-α-induced NF-κB activation in HEK293/NF-κB-luciferase reporter assay.

HEK-293/NF-κB-luc stable cell line (Panomics, Cat #RC0014), an adherent cell, was used in the assay. For sustaining cell culture, the cells were incubated in cell culture dish with DMEM containing 10% FBS at 37° C. with 5% $CO_2$. Sub-culture was performed when cells reached 90% confluence. For the assay, the cells were trypsinized and suspended in culture medium. The cell density was determined and adjusted to $3 \times 10^5$ cells/mL. The cells were then seeded into a 96-well plate and incubated at 37° C. with 5% $CO_2$ overnight.

Two *Andrographis paniculata* extracts, Example 1 and Standard 1, and positive control IKK-2 inhibitor IV (Calbiochem, Cat #401481) were serially diluted in DMSO and further diluted in medium. Diluted solution was added into wells. The final concentrations for Standard 1 and Example 1 were: 300, 120, 48, 19.2, 7.68, 3.07, 1.23 and 0.49 µg/mL. The final concentrations for IKK-2 inhibitor IV were: 10, 4, 1.6, 0.64, 0.26, 0.10, 0.041, and 0.016 µM. The plate was incubated at 37° C. with 5% $CO_2$ for 30 minutes. Stimuli rhTNFα was added into wells and its final concentration was 10 ng/mL. The plate was incubated at 37° C. under 5% $CO_2$ for about 6 hours.

After incubation, the cell supernatant was removed and discarded. Cell lysis buffer was added into each well. The plate was stored at −70° C. for about 20 min, and then the plate was taken out. The cell lysates were thawed and transferred into a 96-well white flat bottom plate. The NF-κB activation was measure by using commercial Steady-Glo® Luciferase Assay System (Promega, Cat #E2520). The luminescence (L) was measured by the instrument Victor3 (Perkin Elmer). The inhibition ratio was calculated as follows:

$$\text{Inhibition Ration (\%)} = \frac{L_{maximum} - L_{test\,sample}}{L_{maximum} - L_{minimum}} \times 100$$

where $L_{test\,sample}$ is the luminescence of cells treated with the test samples and stimuli, $L_{maximum}$ is the luminescence of cells treated with stimuli only, and $L_{minimum}$ is the luminescence of cells treated without test samples and stimuli. $IC_{50}$ of each test sample was calculated by "XLfit"software. The final result was expressed as relative potency by comparing Example 1 with Standard1. The relative potency was calculated as follows:

$$\text{Relative potency (\%)} \times = \frac{IC_{50\,Standard\,1}}{IC_{50\,Example\,1}} \times 100$$

Similarly, other *Andrographis paniculata* extracts ("Example 2-6") were tested. The results showed that Examples 1-6 were much more potent than Standard 1 with the relative potency of 418.5% (Mean) (n=6). The results were shown in Table 3.

TABLE 3

Inhibitory potency on NF-κB activation

| Example # | $IC_{50}$ (µg/mL) | NF-κB activation relative potency % based on Standard 1 |
|---|---|---|
| 1 | 18.5 | 284.4% |
| 2 | 15.4 | 270.5% |
| 3 | 14.8 | 452.2% |
| 4 | 14.6 | 561.7% |
| 5 | 16.4 | 408.2% |
| 6 | 12.5 | 533.9% |

Assay 3: Effects on Pro-Inflammatory Gene Regulation

Cytokines have a crucial role in the pathogenesis of IBD, where they control multiple aspects of the inflammatory response. In particular, the imbalance between pro-inflammatory and anti-inflammatory cytokines in IBD impedes the resolution of inflammation and resulted in disease perpetuation and tissue destruction. Pro-inflammatory cytokines, such as TNF-α, IL-1β, IL-6 and IL-12p40, have demonstrated fundamental roles in controlling mucosal inflammation in the disease. For instance, TNF-α, through activation of NF-κB, receptor-interacting protein kinases and caspase 3 pathways, exerts various pleiotropic pro-inflammatory effects in IBD, including augmented angiogenesis, the induction of Paneth cell death via necroptosis, the production of matrix metalloproteinases by myofibroblasts, and activation of macrophages and effector T cells, and direct damage of intestinal epithelial cells via myosin light chain kinase activation. Members of IL-12 family are produced by antigen presentation cells during intestinal inflammation, perpetuating local Th17 cell responses and suppressing regulatory T cell activity. Therapies based on anti-pro-inflammatory cytokines have been very successful in treatment of various autoimmune diseases, including IBD. For example, infliximab, an anti-TNF-α antibody, has demonstrated great clinical improvement and mucosal healing in moderate to severe IBD patients [Darcy M., et al, Ulcerative Colitis. 2015 Decision resources Group]. In addition, Ustekinumab, a specific antibody for common p40 subunit of IL-12 and IL-23, demonstrated increased clinical response in patients with active CD, particularly for those who fail to respond to anti-TNF therapy [Yu Q H., et al. Crohn's Disease. 2015 Decision Resources Group].

Inhibition of pro-inflammatory cytokine production by Example 1 has been evaluated in LPS-stimulated human PBMCs in vitro. As a control, 5-aminosalicylic acid (5-ASA) has also been evaluated.

Human peripheral blood mononuclear cells (hPBMCs) were isolated from the blood of healthy humans by Ficoll density gradient separation and stored in the liquid nitrogen. For the assay, the cells were thawed from liquid nitrogen and centrifuged. Then the cells were suspended in fresh culture medium (RPMI-1640 with 10% heat-inactivated FBS) and cultured overnight. The cell density was determined and adjusted to $1 \times 10^6$ cells/mL. The cells were then seeded into a 96-well plate and incubated at 37° C. with 5% $CO_2$.

The two *Andrographis paniculata* extracts, Standard 1 and Example 1 were serially diluted in DMSO and further diluted in medium. Diluted solution was added into wells. The plate was incubated at 37° C. with 5% $CO_2$ for 30 minutes until stimuli treatment. LPS or a combination of anti-CD3 monoclonal antibody (mAb) and anti-CD28 mAb was added into the wells. The final concentrations of stimuli were: 1 µg/mL LPS or 1 µg/mL antiCD3 plus 0.5 µg/mL antiCD28 mAb. The plate was incubated at 37° C. under 5% $CO_2$ for about 5 hours. The cells were collected and supernatants were removed. 150 µL RLT buffer was added into each well. The plate was stored at −80° C. until RNA extraction.

Total RNA was extracted using RNeasy 96 kit (QIAGEN) and cDNA was synthesized from the RNA template using High Capacity cDNA RT kit (Applied Biosystems). Quantitative real-time PCR detection of gene expression was effected using SYBR Premix Ex Taq TM II (TakaRa). GAPDH was used as a reference gene (Primer sequences were shown in Table 4). Expression of genes analyzed by q-PCR was normalized to GAPDH using the fold change ($2^{-\Delta\Delta CT}$) method. The formula used in calculation was shown as follows:

$$\text{Fold} = 2^{-\Delta\Delta CT} = 2^{-[(CT_{test\ sample} - CT_{test\ sample\_GAPDH}) - (CT_{minimum} - CT_{minimum\_GAPDH})]}$$

where $CT_{test\ sample}$ is the CT value of target gene in cells treated with the test samples and stimuli; $CT_{test\ sample\text{-}GAPDH}$ is the CT value of GAPDH gene in cells treated with the test samples and stimuli; $CT_{minimum}$ is the CT value of target gene in cells treated without test samples and stimuli, and $CT_{minimum\text{-}GAPDH}$ is the CT value of GAPDH gene in cells treated without test samples and stimuli; The inhibition ratio was calculated as follows:

$$\text{Inhibition Ration}(\%) = \frac{Fold_{Maximum} - Fold_{test\ sample}}{Fold_{Maximum} - Fold_{minimum}} \times 100$$

where $Fold_{test\ sample}$ is the fold value of cells treated with the test samples and stimuli, $Fold_{maximum}$ is the fold value of cells treated with stimuli only, and $Fold_{minimum}$ is the fold of cells treated without test samples and stimuli.

The results indicated that Example 1 significantly suppressed LPS induced mRNA expression of TNFα, IL-1β, IL-6, IL-12p40, IL-18 and Cox2 in a dose-dependent manner in hPBMCs (FIG. 1). Example 1 also inhibited antiCD3 mAb/antiCD28 mAb induced mRNA expression of CCL-20 and IFNγ in hPBMCs (FIG. 2).

Assay 4: Effects on Chemokine Gene Regulation

Chemokines are a group of chemoattractant cytokines that exert double-edged effects on both host defense and inflammation. Pro-inflammatory chemokines released from a wide variety of cells in response to pro-inflammatory stimuli have been shown to play an essential role in the recruitment of leukocytes, such as neutrophils, monocytes and other effector cells from blood to sites of inflammation and tissue damage.

The chemokine CCL-20 and its cognate receptor CCR6 are of particular interest, due to the overexpression of both in IBD patients [Skovdahl H K., et al. Expression of CCL-20 and its corresponding receptor CCR6 is enhanced in active inflammatory bowel disease, and TLR3 mediates CCL-20 expression in colonic epithelial cells. PLoS One. 2015 Nov. 4; 10(11):e0141710]. CCL-20, recently identified as a susceptibility gene for IBD, is expressed by many cell types when stimulated with pro-inflammatory cytokines. CCL-20 has been shown to direct CCR6-expressed effector cells, such as Treg, Th17, B cells and immature dendritic cells, to gut mucosa. Thus, blockade of CCL-20 may provide benefit for the treatment of IBD.

Two adherent epithelial cell lines, HT29 and T84, were used in the assay. For sustaining cell culture, HT29 cells were incubated in cell culture dish with McCoy's 5a Medium containing 10% FBS, and T84 cells were incubated with DMEM/F-12 (1:1) medium containing 5% FBS. All cells were incubated at 37° C. with 5% CO2. Sub-culture was performed when cells reached 90% confluence. For the assay, the cells were trypsinized and suspended in culture medium. The cell density was determined and adjusted to $1 \times 10^6$ cells/mL. The cells were then seeded into a 96-well plate and incubated at 37° C. with 5% $CO_2$ overnight.

The two *Andrographis paniculata* extracts, Standard 1 and Example 1, were serially diluted in DMSO and further diluted in medium. Diluted solution was added into wells. The final concentrations for Standard 1 were: 300, 100, 30 and 10 μg/mL. The final concentrations for Example 1 were: 100, 30, 10 and 1 μg/mL. The plate was incubated at 37° C. with 5% $CO_2$ for 30 minutes until stimuli treatment. Stimuli rhTNFα was added into wells and its final concentration was 50 ng/mL. The plate was incubated at 37° C. with 5% $CO_2$ for about 5 hours. The supernatants were removed, and 150 μL RLT buffer was added into each well. The plate was stored at −80° C. until RNA extraction.

Total RNA was extracted using RNeasy 96 kit (QIAGEN), and cDNA was synthesized from RNA template using High Capacity cDNA RT kit (Applied Biosystems). Quantitative real-time PCR detection of gene expression was using SYBR Premix Ex Taq TM II (TaKaRa). GAPDH was used as a reference gene (Primer sequences were shown in Table 4). Expression of genes analyzed by q-PCR was normalized to GAPDH using the fold change ($2^{-\Delta\Delta CT}$) method. The formula used in calculation was shown as follows:

$$\text{Fold} = 2^{-\Delta\Delta CT} = 2^{-[(CT_{test\ sample} - CT_{test\ sample\_GAPDH}) - (CT_{minimum} - CT_{minimum\_GAPDH})]}$$

where $CT_{test\ sample}$ is the CT value of target gene in cells treated with the test samples and stimuli; $CT_{test\ sample\text{-}GAPDH}$ is the CT value of GAPDH gene in cells treated with the test samples and stimuli; $CT_{minimum}$ is the CT value of target gene in cells treated without test samples and stimuli, and $CT_{minimum\text{-}GAPDH}$ is the CT value of GAPDH gene in cells treated without test samples and stimuli; The inhibition ratio was calculated as follows:

$$\text{Inhibition Ration}(\%) = \frac{Fold_{maximum} - Fold_{test\ sample}}{Fold_{maximum} - Fold_{minimum}} \times 100$$

where $Fold_{test\ sample}$ is the fold value of cells treated with the test samples and stimuli, $Fold_{maximum}$ is the fold value of cells treated with stimuli only, and $Fold_{minimum}$ is the fold of cells treated without test samples and stimuli.

The results indicated that Example 1 significantly inhibited expression of CCL-20, CXCL-9, CXCL-10, CXCL-11 in T84 cells (FIG. 3) and CCL-20, CXCL-10, CXCL-11, CXCL-16 in HT29 cells (FIG. 4).

Assay 5: Effects on Growth Factor Gene Regulation

Mucosal healing has emerged as a key treatment goal in IBD that predicts sustained clinical remission of patients. The structural basis of mucosal healing is an intact barrier function of the gut epithelium that prevents translocation of commensal bacteria into the mucosa and submucosa with subsequent immune cell activation. Thus, mucosal healing should be considered as an initial event in the suppression of inflammation of deeper layers of the bowel wall, rather than as a sign of complete healing of gut inflammation.

Mucosal healing relies on coordinated events consisting of intestinal epithelial cell restitution, proliferation and differentiation, where epidermal growth factor (EGF) plays important roles. Significantly lower levels of serum EGF are observed in IBD patients compared to healthy controls. Interestingly, a short-term treatment using topical recombinant EGF has achieved clinical remission in a clinical trial of UC, suggesting that EGF plays a beneficial role in the treatment of the disease [Huynh E., et al. EGF and EGFR: promising targets for modulating inflammation and mucosal healing therapy in IBD. Inflamm Cell Signal. 2015; 2(3): e840]. In a case report of EGF treatment for IBD-associated pyoderma gangrenosum, daily topical EGF led to significant wound healing within 2 weeks and complete wound closure at 5 months despite rapid tapering of steroids. These investigations suggest that although EGF may not be a mainstay for UC, it may still play a beneficial role in patients with UC [Krishnan K., et al. Intestinal growth factors: potential use in the treatment of inflammatory bowel disease and their role in mucosal healing. Inflammatory Bowel Diseases. 2011; 17(1):410-22].

The fibroblast growth factor family is comprised of at least 18 heparin-binding peptides (FGF1 through FGF18) and oncogenes. FGF1 and FGF2 are commonly referred to as acidic FGF (aFGF) and basic FGF (bFGF) respectively. Members of the FGF family generally act to enhance cell proliferation, modulate cell differentiation, and accelerate cell migration, angiogenesis, and extracellular matrix remodeling. FGF1 is one of the most promising cytokines for treating impaired wound healing. Previous studies have demonstrated that several growth factors including FGF-2 are overexpressed in IBD and their roles in epithelial repair have been postulated. Furthermore, it has been reported that an elevated FGF-2 level in serum of active IBD patients might promote mucosal healing and/or intestinal fibrinogenesis.

Enhancement of EGF and FGF expression were investigated in a human HT-29 and T84 cell lines.

Two adherent epithelial cell lines, HT29 and T84, were used in the assay. For sustaining cell culture, HT29 cells were incubated in cell culture dish with McCoy's 5a Medium containing 10% FBS, and T84 cells were incubated with DMEM/F-12 (1:1) medium containing 5% FBS. All cells were incubated at 37° C. with 5% $CO_2$. Sub-culture was performed when cells reached 90% confluence.

For the assay, the cells were trypsinized and suspended in culture medium. The cell density was determined and adjusted to $1\times10^6$ cells/mL. Then, the cells were seeded into a 96-well plate and incubated at 37° C. with 5% $CO_2$ overnight.

The two *Andrographis paniculata* extracts, Standard 1 and Example 1, were serially diluted in DMSO and further diluted in medium. Diluted solution was added into wells. The final concentrations for Standard 1 were: 300, 100, 30 and 10 µg/mL. The final concentrations for Example 1 were: 100, 30, 10 and 1 µg/mL. The plate was incubated at 37° C. with 5% $CO_2$ for about 24 hours. The supernatants were removed and 150 µL RLT buffer was added into each well. The plate was stored at −80° C. until RNA extraction.

Total RNA was extracted using RNeasy 96 kit (QIAGEN) and cDNA was synthesized from RNA template using High Capacity cDNA RT kit (Applied Biosystems). Quantitative real-time PCR detection of gene expression was using SYBR Premix Ex Taq TM II (TaKaRa). GAPDH was used as a reference gene (Primer sequences were shown in Table 4). Expression of genes analyzed by q-PCR was normalized to GAPDH using the fold change ($2^{-\Delta\Delta CT}$) method. The formula used in the calculation is shown as follows:

$$\text{Fold}=2^{-\Delta\Delta CT}=2^{-[(CT_{test\ sample}-CT_{test\ sample\_GAPDH})-(CT_{minimum}-CT_{minimum\_GAPDH})]}$$

where $CT_{test\ sample}$ is the CT value of target gene in cells treated with the test samples; $CT_{test\ sample\text{-}GAPDH}$ is the CT value of GAPDH gene in cells treated with the test samples; $CT_{minimum}$ is the CT value of target gene in cells treated without test samples, and $CT_{minimum\text{-}GAPDH}$ is the CT value of GAPDH gene in cells treated without test samples.

The results indicated that both Example 1 and AND increased mRNA expression of EGF in HT29 cells and T84 cells (FIG. 5). Example 1 also increased mRNA expression of FGF1 and FGF2 in T84 cells, however, AND alone had no similar effect. It suggested that the up-regulation of FGF1 and FGF2 was AND-independent (FIG. 6).

Similarly, enhancement effects of Example 10 on EGF and FGF1 and FGF2 mRNA expressions in epithelial cell lines HT29 and T84 were tested according to the procedure as described above. The results are shown in FIG. 7 and FIG. 8. Example 10 increased mRNA expression of EGF and FGF1 and FGF2. 100 µg/ml of Example 10 was significantly better than 100 µg/ml of Standard 1.

TABLE 4

Primer sequences

| Target gene | Primer (Forward) | Primer (Reverse) |
| --- | --- | --- |
| human IL-6 | GCCAGAGCTGTGCAGATGAG (SEQ ID NO: 1) | TCAGCAGGCTGGCATTTG (SEQ ID NO: 17) |
| human TNF-a | TGCTTGTTCCTCAGCCTCTT (SEQ ID NO: 2) | CAGAGGGCTGATTAGAGAGAGGT (SEQ ID NO: 18) |
| human COX-2 | CCCTTCTGCCTGACACCTTT (SEQ ID NO: 3) | GTATTTCATCTGCCTGCTCTGGT (SEQ ID NO: 19) |
| human IL-12p40 | CTATGGTGAGCCGTGATTGTG (SEQ ID NO: 4) | CTGTGTCATCCTCCTGTGTCTTTT (SEQ ID NO: 20) |
| human IL-18 | CTTCCAGATCGCTTCCTCTC (SEQ ID NO: 5) | TCAAATAGAGGCCGATTTCC (SEQ ID NO: 21) |
| human IFN-γ | AACTTTAAAGATGACCAGAGCATCC (SEQ ID NO: 6) | TGCGTTGGACATTCAAGTCAG (SEQ ID NO: 22) |
| human IL-1β | TTCGACACATGGGATAACGAGG (SEQ ID NO: 7) | TTTTTGCTGTGAGTCCCGGAG (SEQ ID NO: 23) |
| human CCL20 | TGCTGTACCAAGAGTTTGCTC (SEQ ID NO: 8) | CGCACACAGACAACTTTTTCTTT (SEQ ID NO: 24) |
| human CXCL9 | GCATCATCTTGCTGGTTCTGATTGG (SEQ ID NO: 9) | GCGACCCTTTCTCACTACTGGGGT (SEQ ID NO: 25) |
| human CXCL10 | CCAATTTTGTCCACGTGTTG (SEQ ID NO: 10) | TTCTTGATGGCCTTCGATTC (SEQ ID NO: 26) |

TABLE 4-continued

Primer sequences

| Target gene | Primer (Forward) | Primer (Reverse) |
|---|---|---|
| human CXCL11 | AGAGGACGCTGTCTTTGCAT (SEQ ID NO: 11) | TGGGATTTAGGCATCGTTGT (SEQ ID NO: 27) |
| human CXCL16 | ACTACACGAGGTTCCAGCTCC (SEQ ID NO: 12) | CTTTGTCCGAGGACAGTGATC (SEQ ID NO: 28) |
| human EGF | TGGATGTGCTTGATAAGCGG (SEQ ID NO: 13) | ACCATGTCCTTTCCAGTGTGT (SEQ ID NO: 29) |
| human FGF1 | GATGGCACAGTGGATGGGAC (SEQ ID NO: 14) | AAGCCCGTCGGTGTCCATGG (SEQ ID NO: 30) |
| human FGF2 | GCTCTTAGCAGACATTGGAAG (SEQ ID NO: 15) | GTGTGTGCTAACCGTTACCT (SEQ ID NO: 31) |
| human GAPDH | TCGACAGTCAGCCGCATCTTCTTT (SEQ ID NO: 16) | ACCAAATCCGTTGACTCCGACCTT (SEQ ID NO: 32) |

Assay 6: Effects on Growth Factor Gene Regulation

Enhancement of FGF1 expression of Example 7 and the four ingredients AND, NAND, DAND, and DDAND was investigated in human T84 cell line.

The adherent epithelial cell line T84 was used in the assay. For sustaining cell culture, T84 cells were incubated with DMEM/F-12 (1:1) medium containing 5% FBS at 37° C. with 5% $CO_2$. Sub-culture was performed when cells reached 90% confluence.

For the assay, the cells were trypsinized and suspended in culture medium. The cell density was determined and adjusted to $1 \times 10^6$ cells/mL. Then, the cells were seeded into a 96-well plate and incubated at 37° C. with 5% $CO_2$ overnight.

The two *Andrographis paniculata* extracts, Standard 1 and Example 7, and AND, NAND, DAND, DDAND, and the mixture of them (named as the mixture of 4 markers, wherein the amounts of AND, NAND, DAND, and DDAND were 69%, 11%, 5%, and 15%, respectively, by weight relative to the weight of the mixture) were serially diluted in DMSO and further diluted in medium. Diluted solution was added into wells. The final concentrations for Standard 1 were: 300 and 100 μg/mL. The final concentration for Example 7 was: 100 μg/mL. The final concentration for NAND, DAND and DDAND was 10 μg/mL and AND was 40 μg/mL. The final concentrations for mixture of 4 markers were: 100 and 30 μg/mL. The plate was incubated at 37° C. with 5% $CO_2$ for about 24 hours. The supernatants were removed and 150 μL RLT buffer was added into each well. The plate was stored at −80° C. until RNA extraction.

Total RNA was extracted using RNeasy 96 kit (QIAGEN) and cDNA was synthesized from RNA template using High Capacity cDNA RT kit (Applied Biosystems). Quantitative real-time PCR detection of gene expression was using SYBR Premix Ex Taq TM II (TaKaRa). GAPDH was used as a reference gene (Primer sequences were shown in Table 5). Expression of genes analyzed by q-PCR was normalized to GAPDH using the fold change ($2^{-\Delta\Delta CT}$) method. The formula used in the calculation is shown as follows:

$$\text{Fold} = 2^{-\Delta\Delta CT} = 2^{-[(CT_{test\ sample} - CT_{test\ sample\_GAPDH}) - (CT_{minimum} - CT_{minimum\_GAPDH})]}$$

where $CT_{test\ sample}$ is the CT value of target gene in cells treated with the test samples; $CT_{test\ sample-GAPDH}$ is the CT value of GAPDH gene in cells treated with the test samples; $CT_{minimum}$ is the CT value of target gene in cells treated without test samples, and $CT_{minimum-GAPDH}$ is the CT value of GAPDH gene in cells treated without test samples.

The results are shown in FIG. 9. Similar to Example 10, Example 7 up-regulated the expression of FGF1 mRNA. 100 μg/ml of Example 7 was better than 100 μg/ml of Standard 1. The individual compounds, AND, NAND, DAND, DDAND, did not show similar FGF1 up-regulation effect. And the mixture of the 4 compounds slightly up-regulated the expression of FGF1 at 100 μg/ml, but the effect was remarkably weaker compared with 100 μg/ml of Example 7.

TABLE 5

Primer sequences

| Target gene | Primer (Forward) | Primer (Reverse) |
|---|---|---|
| human FGF1 | GATGGCACAGTGGATGGGAC (SEQ ID NO: 33) | AAGCCCGTCGGTGT CCATGG (SEQ ID NO: 35) |
| human GAPDH | TCGACAGTCAGCCGCATCTTCTTT (SEQ ID NO: 34) | ACCAAATCCGTTGA CTCCGACCTT (SEQ ID NO: 36) |

Assay 7: The In Vivo Efficacy of *Andrographis* Extract in a DNBS-Induced Rat Colitis Prophylactic Model
1. Materials
1.1. Test Compounds and Formulation Methods
Test articles: Two *Andrographis paniculata* extracts, Example 10 used in Experiment 1 and Example 11 used in Experiment 2.
Control drugs: Standard 1; and Sulfasalazine (SASP), Sigma-Aldrich, Cat S0883.

Oral suspension of the test articles and Standard 1 were prepared as follows: the test articles and Standard 1 were respectively weighed and added into a 50 mL centrifuge tube. 0.5% sodium carboxymethylcellulose (0.5% CMC-Na) was added. Sonicate for 15 min to give suspensions with desired concentration. The fresh-made formulation was stored away from light, and homogenized thoroughly before use. The administration volume was 10 ml/kg.

Oral suspension of SASP was prepared as follows: SASP was weighed and added into a 50 mL centrifuge tube. 0.5% CMC-Na was added. Sonicate for 15 min to give 30 mg/mL suspension. The fresh-made formulation was stored away from light, and homogenized thoroughly before use. The administration volume was 10 ml/kg.

1.2. Animals:

Male Wistar rats, 110-130 g, were purchased from Shanghai SLAC Laboratory Animal Co. Ltd.

1.3. Reagents

DNBS (2,4-dinitrobenzenesulfonate acid): Cat: D2275, Tokyo Kasei kogyo (Japan).

Sodium Carboxymethylcellulose (CMC-Na): Cat: C9481, Sigma-Aldrich.

Zoletil: Tiletamine-zolazepam; Virbac S.A., Garros, France.

Xylazine: Jilin Huamu Animal Health Product Co., Ltd. Veterinary drug production No. (2015) 070011777.

2. Methods 2.1. Grouping and Dosing Regimen

Histopathology analysis: Proximal colon with obvious ulcer was made into Swiss Rolls, fixed in 10% neutral formalin solution, dehydrated with xylene, embedded in paraffin, sectioned, and stained with hematoxylin and eosin (H&E). The criterion of histopathological assessment of the tissue section was made according to reference (David Prescott, BSc, et al. Loss of Phosphoinositide 3-Kinase p110γ is Protective in the Acute Phase but Detrimental in the Resolution Phase of Hapten-Induced Colitis, Inflamm Bowel Dis. Volume 19, Number 3, March 2013). The severity of lesion was graded based on a semi-quantitative scale using the sum of scores of the following 10 evaluation indicators (see table 7).

TABLE 6

Treatment groups and dosing regimen of the extracts on DNBS induced rat colitis model

| Groups | N | Dose (mg/kg) | Dosing regimen | Route | Vehicle |
|---|---|---|---|---|---|
| Experiment 1 | | | | | |
| Naive (30% ethanol control) | 8 | — | — | — | — |
| Vehicle (DNBS control) | 8 | 0 | Animals were administered 2 h before and 4 h after model induction on the first day and then administered once daily in the next 5 days. | PO | 0.5% CMC-Na |
| DNBS + SASP 300 mg/kg | 8 | 300 | | PO | 0.5% CMC-Na |
| DNBS + "Example 10" 5 mg/kg | 8 | 5 | | PO | 0.5% CMC-Na |
| DNBS + "Example 10" 10 mg/kg | 8 | 10 | | PO | 0.5% CMC-Na |
| DNBS + "Example 10" 20 mg/kg | 8 | 20 | | PO | 0.5% CMC-Na |
| DNBS + "Example 10" 40 mg/kg | 8 | 40 | | PO | 0.5% CMC-Na |
| Experiment 2 | | | | | |
| Naive (30% ethanol control) | 8 | — | — | — | — |
| Vehicle (DNBS control) | 8 | 0 | Animals were administered 2 h before and 4 h after model induction on the first day and then administered once daily in the next 5 days. | PO | 0.5% CMC-Na |
| DNBS + "Example 11" | 8 | 40 | | PO | 0.5% CMC-Na |
| DNBS + Standard 1 | 8 | 130 | | PO | 0.5% CMC-Na |

*SASP group: The animals in the SASP treated group were administered with vehicle 2 h before and with SASP 4 hours after the model induction on the first day and then administrated once daily in the next five days.

2.2. Model Induction

Wistar rats were randomized assigned. The fasting rats were anesthetized with 25 mg/kg Zoletil and 0.5 mg/kg xylazine. And colitis was induced by intracolonic administration of 10 mg or 12 mg DNBS dissolved in 0.25 mL of 30% ethanol (v/v). The animals in naive control group were instilled with 30% ethanol only.

2.3. Assessment

Body weight: Body weights of animals were checked daily on and after grouping.

Diarrhea score: Stool consistency of the animals was monitored and scored daily from the $3^{rd}$ day after the model induction. Evaluation criteria: 0=formed, 1=moist/sticky, 2=loose, 3=liquid.

Colon weight and length measurement: Rats were sacrificed 4 h post the last dosing on the $6^{th}$ day. The abdomen was opened by a midline incision. Adhesion degree of colon and other organs was observed. The colon (from cecum end to the anus) was emptied of its content, rinsed with saline. The weight and length of the colon were measured, and then the colon ratio (colon weight/colon length) was calculated.

TABLE 7

Scoring System for assessing pathologic changes of colon

| Evaluation indicators | Score Assigned |
|---|---|
| Total area affected | None:0 |
| | 25%: 1 |
| | 25%-50%: 2 |
| | 50%-75%: 3 |
| | 75%: 4 |
| Degree of erosion or ulcer | None: 0 |
| | Mild: 1 |
| | Moderate: 2 |
| | Severe: 3 |
| Severe destruction for erosion (%) | None: 0 |
| | 25%: 1 |
| | 25%-50%: 2 |
| | 50%-75%: 3 |
| | 75%: 4 |
| Degree of mucosa edema | Normal: 0 |
| | Mild: 1 |
| | Moderate: 2 |
| | Extensive: 3 |
| Degree of cellular infiltrate | Normal: 0 |
| | Mild: 1 |
| | Moderate: 2 |
| | Severe/transmural: 3 |
| Severely affected in infiltration (%) | None: 0 |
| | 25%: 1 |
| | 25%-50%: 2 |
| | 50%-75%: 3 |
| | 75%: 4 |

TABLE 7-continued

Scoring System for assessing pathologic changes of colon

| Evaluation indicators | Score Assigned |
|---|---|
| Epithelium hyperplasia | None: 0 |
|  | 5%: 1 |
|  | 5%-25%: 2 |
|  | 25%-50%: 3 |
|  | 50%: 4 |
| Muscle thickening | Normal: 0 |
|  | Mild: 1 |
|  | Moderate: 2 |
|  | Extensive: 3 |
| Crypt abscesses | Absent: 0 |
|  | Present: 1 |
| Goblet cell depletion | Absent: 0 |
|  | Present: 1 |

2.4. Statistical Analysis

All of the data were presented as mean±SD.

Body weight data were analyzed with repeated-measures ANOVA analysis by GraphPad Prism 6.0 software. Fisher's Least Significant Difference (LSD) test was used to perform significance analysis. p value was calculated. *p<0.05 refers to significant difference between vehicle control group and each of the treated groups. **p<0.01 refers to extremely significant difference between vehicle control group and each of the treated groups.

The colon ratio inhibition of each animal was calculated by the following formula, wherein CW refers to colon weight, CL refers to colon length:

$$\text{Colon ratio inhibition (\%)} = \frac{CW/CL(\text{vehicle control}) - CW/CL(\text{test article})}{CW/CL(\text{vehicle control}) - CW/CL(\text{naive article})} \times 100\%$$

The statistical analysis of the data of colon length and colon ratio was performed by Graphpad Prism 6.0 software. Unpaired t test or Mann-Whitney test were applied to analyze the significance analysis between test article treated groups and vehicle treated group, based on the normality of the data.

The difference of diarrhea score and histopathology score between vehicle control group and test article treated groups was analyzed with Mann-Whitney test by GraphPad Prism 6.0 software. *p<0.05 refers to statistically significant difference between vehicle control group and each of the treated groups. **p<0.01 refers to extremely statistically significant difference between vehicle control group and each of the treated groups.

3. Result and Discussion 3.1 The Efficacy of the Extracts on the Diarrhea Score and Body Weight in the DNBS Induced Colitis Rat Severe diarrhea was occurred on the $2^{nd}$ day and lasted to the $4^{th}$ day of the model induction and then was recovered gradually. Diarrhea score was measured on the $3^{rd}$ day of model induction. The extracts treated groups at the dose of 40 mg/kg ameliorated the disease progression and alleviated the diarrhea score from the $3^{rd}$ day to the $6^{th}$ day, and even, relieved the diarrhea severity on the $3^{rd}$ day and $4^{th}$ day, the efficacy of which was superior to the efficacy of the positive control SASP treated group at 300 mg/kg/day and Standard 1 treated group at 130 mg/kg/day.

Compared with the naive control group, the Wistar rats in the vehicle control group showed a significant decrease in the growth trend of body weight from the $2^{nd}$ day of model induction. The extracts (5~40 mg/kg/day) restored body weight to a certain extent. The efficacy of the extracts was comparable to positive drug SASP at 300 mg/kg/day and Standard 1 at 130 mg/kg/day.

The oral administration of the extracts at 5~40 mg/kg ameliorated the severity of DNBS-induced colitis model in a certain dose-dependent manner. The extracts at 40 mg/kg/day showed the most remarkable efficacy in the model.

3.2 The Efficacy of the Extracts on Colon Ratio in the DNBS Induced Colitis Rat

The following data showed that the colon ratios in the extracts of the invention treated groups were significantly decreased at the end of the study (Table 8). The colon ratio in the extract treatment groups at 20 mg/kg/day and 40 mg/kg/day were reduced to about 40%, which is comparable with the efficacy of SASP at 300 mg/kg/day and Standard 1 at 130 mg/kg/day.

TABLE 8

Colon length, colon weight and colon ratio in the DNBS induced colitis model

| Groups | Dose (mg/kg) | n | Colon ration CW/CL (%) | Colon ratio inhibition, % |
|---|---|---|---|---|
| Experiment 1 | | | | |
| Naive (ethanol control) | — | 8 | 0.0690 ± 0.0028*** | — |
| Vehicle (DNBS control) | — | 8 | 0.0972 ± 0.0114 | — |
| DNBS + SASP | 300 | 8 | 0.0846 ± 0.0089* | 44.5 |
| DNBS + "Example 10" | 5 | 8 | 0.0930 ± 0.0102 | 14.8 |
|  | 10 | 8 | 0.0892 ± 0.0067 | 28.3 |
|  | 20 | 8 | 0.0872 ± 0.0069* | 35.2 |
|  | 40 | 8 | 0.0867 ± 0.0078* | 37.1 |
| Experiment 2 | | | | |
| Naive (ethanol control) | — | 8 | 0.0741 ± 0.0068*** | — |
| Vehicle (DNBS control) | — | 8 | 0.1033 ± 0.0077 | — |
| DNBS + "Example 11" | 40 | 8 | 0.0890 ± 0.0065** | 48.9 |
| DNBS + Standard 1 | 130 | 8 | 0.0929 ± 0.0083* | 35.6 |

*p < 0.05 vs vehicle control,
**p < 0.01 vs vehicle control,
***p < 0.001 vs vehicle control.

3.3 The Efficacy of the Extracts on the Histopathology in the DNBS Induced Colitis Model All the samples in the naive control group showed focal inflammatory cell infiltration without mucosa erosion. In vehicle control group, seven samples showed pathological changes including severe mucosal erosion, severely damaged mucosa structure, inflammatory cell infiltration and even be seen throughout the whole intestinal wall, mucosa edema and muscle thickening. One sample showed very mild pathological changes with only focal inflammatory cell infiltration. In SASP (300 mg/kg/day) group, five samples showed severe mucosal erosion and inflammatory cell infiltration. Three samples showed only focal cell infiltration without obvious mucosa erosion. Mucosa edema was found in most samples in this group. In the extracts (10 mg/kg/day, 20 mg/kg/day and 40 mg/kg/day) treated groups, five samples in each group showed moderate to severe mucosal erosion, inflammatory cell infiltration, and mucosa edema. The other three samples in each group showed only inflammatory cell infiltration without obvious mucosa erosion. Mucosa edema was found in all samples.

By histopathological score evaluation, significant decreased histological score was found in the extracts treated groups at 10 mg/kg/day, 20 mg/kg/day and 40 mg/kg/day compared with vehicle control group, wherein the histological score of the Example 10 treated group at 40 mg/kg/day is comparable with the score of SASP treated group at 300 mg/kg/day. Significant improvement in histological changes of DNBS induced colitis model were shown in the extract treated groups at 20 mg/kg/day and 40 mg/kg/day, mainly in reducing ulcer area and % Severe destruction, inflammatory cell infiltration, mucosa edema, and muscle thickening. (Table 9)

TABLE 9

The efficacy of the extracts on the colon histopathology score in the DNBS induced rat colitis model

| Group | Dose (mg/kg) | n | Total area affected (%) | Degree of erosion/ulcer | Severe destruction for erosion (%) | Degree of mucosa edema | Degree of cellular infiltrate | Severely affected in cellular infiltration (%) |
|---|---|---|---|---|---|---|---|---|
| Experiment 1 | | | | | | | | |
| Naive (ethanol control) | — | 8 | 1.0 ± 0.0 | 0.0 ± 0.0 | 0.0 ± 0.0 | 0.8 ± 0.5 | 1.8 ± 0.7 | 1.0 ± 0.0 |
| Vehicle (DNBS control) | — | 8 | 2.5 ± 1.2 | 2.6 ± 1.1 | 1.3 ± 0.7 | 2.4 ± 1.1 | 2.5 ± 0.8 | 2.1 ± 0.6 |
| DNBS + SASP | 300 | 8 | 1.6 ± 0.7 | 1.6 ± 1.4 | 0.8 ± 0.7 | 1.6 ± 0.9 | 2.1 ± 0.8 | 1.6 ± 0.7 |
| DNBS + Example 10 | 5 | 8 | 2.1 ± 0.8 | 2.5 ± 1.1 | 1.0 ± 0.5 | 2.5 ± 0.8 | 2.5 ± 0.5 | 1.9 ± 0.6 |
| | 10 | 8 | 1.6 ± 0.7 | 1.9 ± 1.6 | 0.6 ± 0.5 | 2.1 ± 1.0 | 2.3 ± 0.7 | 1.5 ± 0.8 |
| | 20 | 8 | 1.9 ± 0.8 | 1.9 ± 1.6 | 0.6 ± 0.5 | 1.8 ± 0.7 | 2.1 ± 0.6 | 1.6 ± 0.9 |
| | 40 | 8 | 1.5 ± 0.5 | 1.8 ± 1.5 | 0.6 ± 0.5 | 1.9 ± 1.0 | 2.4 ± 0.5 | 1.3 ± 0.5 |

| Group | Dose (mg/kg) | Epithelium hyperplasia | Muscle thickening | Crypt abscesses | Goblet cell depletion | The sum of score |
|---|---|---|---|---|---|---|
| Experiment 1 | | | | | | |
| Naive (ethanol control) | — | 0.8 ± 0.5 | 0.9 ± 0.4 | 0.0 ± 0.0 | 0.6 ± 0.5 | 6.8 ± 1.9** |
| Vehicle (DNBS control) | — | 0.9 ± 0.4 | 1.8 ± 1.0 | 0.3 ± 0.5 | 0.9 ± 0.4 | 17.1 ± 6.3 |
| DNBS + SASP | 300 | 0.8 ± 0.5 | 1.4 ± 0.9 | 0.1 ± 0.4 | 0.9 ± 0.4 | 12.5 ± 6.3* |
| DNBS + Example 10 | 5 | 1.0 ± 0.0 | 2.3 ± 0.7 | 0.3 ± 0.5 | 1.0 ± 0.0 | 17.0 ± 3.7 |
| | 10 | 0.9 ± 0.4 | 1.6 ± 1.1 | 0.1 ± 0.4 | 0.9 ± 0.4 | 13.5 ± 5.6* |
| | 20 | 0.9 ± 0.4 | 1.4 ± 0.5 | 0.1 ± 0.4 | 0.9 ± 0.4 | 13.1 ± 5.0* |
| | 40 | 1.0 ± 0.0 | 1.0 ± 0.5 | 0.1 ± 0.4 | 1.0 ± 0.0 | 12.5 ± 3.7** |

*$p < 0.05$ vs vehicle control,
**$p < 0.01$ vs vehicle control.

---

What is claimed is:

1. An extract of *Andrographis paniculata*, comprising at least 50.0% total andrographolide lactones by weight relative to the weight of the extract, wherein the total andrographolide lactones comprise AND, NAND, DAND, and DDAND, in amounts ranging from 20.0 to 50.0%, 2.0 to 15.0%, 0.5 to 6.0%, and 5.0 to 20.0%, respectively, by weight relative to the weight of the extract.

2. The extract of claim 1, wherein, the amount of total andrographolide lactones ranges from 55.0 to 75.0% by weight relative to the weight of the extract, wherein the total andrographolide lactones comprise AND, NAND, DAND, and DDAND, in amounts ranging from 20.0 to 50.0%, 4.0 to 15.0%, 0.5 to 6.0%, and 5.0 to 15.0%, respectively, by weight relative to the weight of the extract.

3. The extract of claim 1, wherein the amount of total andrographolide lactones ranges from 55.0 to 75.0% by weight relative to the weight of the extract, wherein the total andrographolide lactones comprise AND, NAND, DAND, and DDAND, in amounts ranging from 25.0 to 45.0%, 4.0 to 12.0%, 1.0 to 5.0%, and 5.0 to 10.0%, respectively, by weight relative to the weight of the extract.

4. The extract of claim 1, wherein the amount of total andrographolide lactones ranges from 55.0 to 75.0% by weight relative to the weight of the extract, wherein the total andrographolide lactones comprise AND, NAND, DAND, and DDAND, in amounts ranging from 30.0 to 45.0%, 6.0 to 10.0%, 1.0 to 5.0%, and 5.0 to 10.0%, respectively, by weight relative to the weight of the extract.

5. A process for preparing the extract of claim 1, comprising the steps:
   (a) refluxing the dried aerial part of *Andrographis paniculata* with 80%-95% ethanol to provide a first ethanol extract;
   (b) adding dextrin to the first ethanol extract, and drying the resulting mixture to obtain a first solid;
   (c) extracting the first solid with 90-100% ethanol, collecting the ethanol phase and decolorizing it with activated charcoal, collecting the liquid phase, and removing the solvent to provide a second solid; and
   (d) washing the second solid with a weakly polar or non-polar organic solvent, and collecting the resulting solid residue to provide the extract of *Andrographis paniculate,*
   wherein the process further comprises the step of:
   (i) before step (d), washing the second solid with water and collecting the resulting solid residue; or
   (ii) before step (c), washing the first solid with water and collecting the resulting solid residue.

6. The extract of *Andrographis paniculata* according to claim 1, prepared by a process comprising the steps:
   (a) refluxing the dried aerial part of *Andrographis paniculata* with 80%-95% ethanol to provide a first ethanol extract;
   (b) adding dextrin to the first ethanol extract, and drying the resulting mixture to obtain a first solid;
   (c) extracting the first solid with 90-100% ethanol, collecting the ethanol phase and decolorizing it with activated charcoal, collecting the liquid phase, and removing the solvent to provide a second solid;
   (d) washing the second solid with water and collecting the resulting solid residue; and
   (e) washing the solid residue with a weakly polar or non-polar organic solvent, and collecting the resulting solid residue to provide the extract of *Andrographis paniculata*.

7. The extract of *Andrographis paniculata* according to claim 1, prepared by a process comprising the steps:
   (a) refluxing the dried aerial part of *Andrographis paniculata* with 80%-95% ethanol to provide a first ethanol extract;
   (b) adding dextrin to the first ethanol extract, and drying the resulting mixture to obtain a first solid;
   (c) washing the first solid with water, and collecting the resulting solid residue;
   (d) extracting the solid residue with 90-100% ethanol, collecting the ethanol phase and decolorizing it with activated charcoal, collecting the liquid phase, and removing the solvent to provide a second solid;
   (e) washing the second solid with a weakly polar or non-polar organic solvent, and collecting the resulting solid residue to provide the extract of *Andrographis paniculata*.

8. A pharmaceutical composition comprising an extract of claim 1 and a pharmaceutically acceptable excipient.

9. A method of treating autoimmunity and inflammatory disease in a subject, comprising administering to the subject in need thereof a therapeutically effective amount of a pharmaceutical composition of claim 8.

10. The method of claim 9, wherein the autoimmunity and inflammatory disease is selected from rheumatoid arthritis (RA), inflammatory bowel disease (IBD), psoriasis, systemic lupus erythematosus (SLE), asthma, and chronic obstructive pulmonary disease (COPD).

11. The method of claim 9, wherein the inflammatory bowel disease is ulcerative colitis or Crohn's Disease.

12. The process of claim 5, wherein step (a) comprises refluxing the dried aerial part of *Andrographis paniculata* with 80%-95% ethanol twice.

13. The process of claim 5, wherein step (a) comprises (i) refluxing the dried aerial part of *Andrographis paniculata* with 80%-95% ethanol, (ii) extracting the solid residue with additional 80%-95% ethanol, (iii) combining the ethanol phases, and (iv) removing the solvent to provide the first ethanol extract.

14. The process of claim 5, wherein step (a) comprises (i) refluxing the dried aerial part of *Andrographis paniculata* with 80%-95% ethanol, (ii) extracting the solid residue with additional 80%-95% ethanol, (iii) combining the ethanol phases, and (iv) removing the solvent to provide the first ethanol extract.

15. An extract of *Andrographis paniculata* prepared by the process of claim 5.

\* \* \* \* \*

SEQUENCE LISTING

<160> NUMBER OF SEQ ID NOS: 36

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
gccagagctg tgcagatgag                    20

```
<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
tgcttgttcc tcagcctctt                                                    20

<210> SEQ ID NO 3
<211> LENGTH: 20
<212> TYPE: DNA
<213> ORGANISM: Artificial
<220> FEATURE:
<223> OTHER INFORMATION: primer

<400> SEQUENCE: 3
cccttctgcc tgacaccttt                                                    20

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
ctatggtgag ccgtgattgt g                                                  21

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
cttccagatc gcttcctctc                                                    20

<210> SEQ ID NO 6
<211> LENGTH: 25
<212> TYPE: DNA
<213> ORGANISM: Artificial
<220> FEATURE:
<223> OTHER INFORMATION: primer

<400> SEQUENCE: 6
aactttaaag atgaccagag catcc                                              25

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
ttcgacacat gggataacga gg                                                 22

<210> SEQ ID NO 8
<211> LENGTH: 21
<212> TYPE: DNA
<213> ORGANISM: Artificial
<220> FEATURE:
<223> OTHER INFORMATION: primer
```

<400> SEQUENCE: 8
tgctgtacca agagtttgct c                21

<210> SEQ ID NO 9
<211> LENGTH: 25
<212> TYPE: DNA
<213> ORGANISM: Artificial
<220> FEATURE:
<223> OTHER INFORMATION: primer

<400> SEQUENCE: 9
gcatcatctt gctggttctg attgg            25

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10
ccaattttgt ccacgtgttg                  20

<210> SEQ ID NO 11
<211> LENGTH: 20
<212> TYPE: DNA
<213> ORGANISM: Artificial
<220> FEATURE:
<223> OTHER INFORMATION: primer

<400> SEQUENCE: 11
agaggacgct gtctttgcat                  20

<210> SEQ ID NO 12
<211> LENGTH: 21
<212> TYPE: DNA
<213> ORGANISM: Artificial
<220> FEATURE:
<223> OTHER INFORMATION: primer

<400> SEQUENCE: 12
actacacgag gttccagctc c                21

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
tggatgtgct tgataagcgg                  20

<210> SEQ ID NO 14
<211> LENGTH: 20
<212> TYPE: DNA
<213> ORGANISM: Artificial
<220> FEATURE:
<223> OTHER INFORMATION: primer

<400> SEQUENCE: 14
gatggcacag tggatgggac                  20

```
<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15
gctcttagca gacattggaa g                                              21

<210> SEQ ID NO 16
<211> LENGTH: 24
<212> TYPE: DNA
<213> ORGANISM: Artificial
<220> FEATURE:
<223> OTHER INFORMATION: primer

<400> SEQUENCE: 16
tcgacagtca gccgcatctt cttt                                           24

<210> SEQ ID NO 17
<211> LENGTH: 18
<212> TYPE: DNA
<213> ORGANISM: Artificial
<220> FEATURE:
<223> OTHER INFORMATION: primer

<400> SEQUENCE: 17
tcagcaggct ggcatttg                                                  18

<210> SEQ ID NO 18
<211> LENGTH: 23
<212> TYPE: DNA
<213> ORGANISM: Artificial
<220> FEATURE:
<223> OTHER INFORMATION: primer

<400> SEQUENCE: 18
cagagggctg attagagaga ggt                                            23

<210> SEQ ID NO 19
<211> LENGTH: 23
<212> TYPE: DNA
<213> ORGANISM: Artificial
<220> FEATURE:
<223> OTHER INFORMATION: primer

<400> SEQUENCE: 19
gtatttcatc tgcctgctct ggt                                            23

<210> SEQ ID NO 20
<211> LENGTH: 24
<212> TYPE: DNA
<213> ORGANISM: Artificial
<220> FEATURE:
<223> OTHER INFORMATION: primer

<400> SEQUENCE: 20
ctgtgtcatc ctcctgtgtc tttt                                           24

<210> SEQ ID NO 21
<211> LENGTH: 20
<212> TYPE: DNA
<213> ORGANISM: Artificial
<220> FEATURE:
<223> OTHER INFORMATION: primer
```

```
<400> SEQUENCE: 21
tcaaatagag gccgatttcc                                              20

<210> SEQ ID NO 22
<211> LENGTH: 21
<212> TYPE: DNA
<213> ORGANISM: Artificial
<220> FEATURE:
<223> OTHER INFORMATION: primer

<400> SEQUENCE: 22
tgcgttggac attcaagtca g                                            21

<210> SEQ ID NO 23
<211> LENGTH: 21
<212> TYPE: DNA
<213> ORGANISM: Artificial
<220> FEATURE:
<223> OTHER INFORMATION: primer

<400> SEQUENCE: 23
tttttgctgt gagtcccgga g                                            21

<210> SEQ ID NO 24
<211> LENGTH: 23
<212> TYPE: DNA
<213> ORGANISM: Artificial
<220> FEATURE:
<223> OTHER INFORMATION: primer

<400> SEQUENCE: 24
cgcacacaga caacttttc ttt                                           23

<210> SEQ ID NO 25
<211> LENGTH: 24
<212> TYPE: DNA
<213> ORGANISM: Artificial
<220> FEATURE:
<223> OTHER INFORMATION: primer

<400> SEQUENCE: 25 gcgaccctt ctcactactg gggt                                          24

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
ttcttgatgg ccttcgattc                                              20

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
tgggatttag gcatcgttgt                                              20
```

```
<210> SEQ ID NO 28
<211> LENGTH: 21
<212> TYPE: DNA
<213> ORGANISM: Artificial
<220> FEATURE:
<223> OTHER INFORMATION: primer

<400> SEQUENCE: 28
ctttgtccga ggacagtgat c                                           21

<210> SEQ ID NO 29
<211> LENGTH: 21
<212> TYPE: DNA
<213> ORGANISM: Artificial
<220> FEATURE:
<223> OTHER INFORMATION: primer

<400> SEQUENCE: 29
accatgtcct ttccagtgtg t                                           21

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
aagcccgtcg gtgtccatgg                                             20

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
gtgtgtgcta accgttacct                                             20

<210> SEQ ID NO 32
<211> LENGTH: 24
<212> TYPE: DNA
<213> ORGANISM: Artificial
<220> FEATURE:
<223> OTHER INFORMATION: primer

<400> SEQUENCE: 32
accaaatccg ttgactccga cctt                                        24

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
gatggcacag tggatgggac                                             20

<210> SEQ ID NO 34
<211> LENGTH: 24
<212> TYPE: DNA
<213> ORGANISM: Artificial
<220> FEATURE:
<223> OTHER INFORMATION: primer
```

```
<400> SEQUENCE: 34
tcgacagtca gccgcatctt cttt                                              24

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
aagcccgtcg gtgtccatgg                                                   20

<210> SEQ ID NO 36
<211> LENGTH: 24
<212> TYPE: DNA
<213> ORGANISM: Artificial
<220> FEATURE:
<223> OTHER INFORMATION: primer

<400> SEQUENCE: 36
accaaatccg ttgactccga cctt                                              24
```